United States Patent
Tylus et al.

(10) Patent No.: US 10,418,639 B2
(45) Date of Patent: Sep. 17, 2019

(54) NON-NOBLE METAL ELECTROCATALYSTS FOR OXYGEN DEPOLARIZED CATHODES AND THEIR USES

(71) Applicant: Northeastern University, Boston, MA (US)

(72) Inventors: Urszula Tylus, Arlington, MA (US); Sanjeev Mukerjee, Mansfield, MA (US); Elise Miner, Milton, GA (US); Kara Strickland, Boston, MA (US)

(73) Assignee: Northeastern University, Boston, MA (US)

( * ) Notice: Subject to any disclaimer, the term of this patent is extended or adjusted under 35 U.S.C. 154(b) by 395 days.

(21) Appl. No.: 14/758,857

(22) PCT Filed: Jan. 7, 2014

(86) PCT No.: PCT/US2014/010502
§ 371 (c)(1),
(2) Date: Jul. 1, 2015

(87) PCT Pub. No.: WO2014/107726
PCT Pub. Date: Jul. 10, 2014

(65) Prior Publication Data
US 2015/0340705 A1    Nov. 26, 2015

Related U.S. Application Data

(60) Provisional application No. 61/844,571, filed on Jul. 10, 2013, provisional application No. 61/749,650, (Continued)

(51) Int. Cl.
*H01M 4/88* (2006.01)
*H01M 4/86* (2006.01)
(Continued)

(52) U.S. Cl.
CPC ............ *H01M 4/88* (2013.01); *C07F 15/025* (2013.01); *C25B 1/26* (2013.01); *C25B 1/34* (2013.01);
(Continued)

(58) Field of Classification Search
CPC .... H01M 4/88; H01M 4/8652; H01M 4/9008; H01M 4/9016; H01M 8/086; C25B 1/26;
(Continued)

(56) References Cited

U.S. PATENT DOCUMENTS 6,066,248 A * 5/2000 Lyke .................. C25B 1/26
                                                    205/620
2003/0222023 A1   12/2003 Mueller et al.
(Continued)

OTHER PUBLICATIONS

D. Zhao, et al., "Iron imidazolate framework as precursor for electrocatalysts in polymer electrolyte membrane fuel cells", Chemical Science, (2012), vol. 3, No. 11, pp. 3200-3205.
(Continued)

*Primary Examiner* — Helen Oi K Conley
(74) *Attorney, Agent, or Firm* — Verrill Dana LLP

(57) ABSTRACT

Highly anion resistant electrocatalysts suitable for catalyzing an oxygen reduction reaction (ORR) and methods of synthesizing the same are provided. The catalysts contain a transition metal, a heteroatom, and carbon. Preferred catalysts include N as the heteroatom and Fe as the transition metal, with active sites having Fe—$N_4$ stoichiometry ($Fe_x$-$N_yC_z$) as part of a metal organic framework (MOF) or sequestered within a MOF. Electrocatalysts further including Fe nanoparticles ($Fe_{NPs}$) are also provided. The catalysts described herein are applicable in the preparation of oxygen decoupled cathodes (ODC) for chlorine evolution processes such as in chlor-alkali cells or HCl electrolyzers. The
(Continued)

catalysts are also useful in preparing ODC for use in fuel cells, including phosphoric acid fuel cells.

25 Claims, 40 Drawing Sheets

Related U.S. Application Data filed on Jan. 7, 2013, provisional application No. 61/750,118, filed on Jan. 8, 2013, provisional application No. 61/767,957, filed on Feb. 22, 2013.

(51) Int. Cl.
*C25B 1/34* (2006.01)
*C07F 15/02* (2006.01)
*C25B 11/04* (2006.01)
*C25B 1/26* (2006.01)
*H01M 4/90* (2006.01)
*H01M 8/086* (2016.01)

(52) U.S. Cl.
CPC .......... *C25B 11/04* (2013.01); *C25B 11/0489* (2013.01); *H01M 4/8652* (2013.01); *H01M 4/8657* (2013.01); *H01M 4/9008* (2013.01); *H01M 4/9016* (2013.01); *H01M 4/9041* (2013.01); *H01M 8/086* (2013.01); *H01M 2004/8689* (2013.01); *H01M 2300/0008* (2013.01)

(58) Field of Classification Search
CPC ....... C25B 1/34; C25B 11/04; C25B 11/0489; C07F 15/025
See application file for complete search history.

(56) References Cited

U.S. PATENT DOCUMENTS

| | | |
|---|---|---|
| 2010/0075123 A1 | 3/2010 | Masel et al. |
| 2012/0077092 A1 | 3/2012 | Lee et al. |
| 2012/0077667 A1 | 3/2012 | Liu et al. |
| 2012/0149560 A1 | 6/2012 | Lee et al. |
| 2013/0157843 A1* | 6/2013 | Muhler .................. B01J 31/06 502/159 |

OTHER PUBLICATIONS

E. Proietti, et al., "Iron-based cathode catalyst with enhanced power density in polymer electrolyte membrane fuel cells", Nature Communications, Aug. 2, 2011, vol. 2, No. 416, 9 pgs.
H. Bux, et al., "Zeolitic Imidazolate Framework Membrane with Molecular Sieving Properties by Microwave-Assisted Solvothermal Synthesis", Journal of the American Chemical Society, (2009), vol. 131, No. 44, pp. 16000-16001.
Y. Pan, et al., "Rapid synthesis of zeolitic imidazolate framework-8 (ZIF-8) nanocrystals in an aqueous system", Chemical Communications, Jan. 1, 2011, vol. 47, No. 7, pp. 2701-2073.
J. Tian, et al., Optimized Synthesis of Fe/N/C Cathode Catalysts for PEM Fuel Cells: A Matter of Iron-Ligand Coordination Strength, Angewandte Chemie International Ecition, May 29, 2013, vol. 125, pp. 7005-7008.

\* cited by examiner

Basolite Z1200

| Wavenumber (cm$^{-1}$) | Peak Intensity | Baseline Intensity | %Intensity increase from Basolite Z1200 |
|---|---|---|---|
| 995.235 | 0.052 | -0.010 | -- |
| 1091.672 | -0.009 | -0.013 | -- |
| 1145.677 | 0.160 | -0.009 | -- |

Fe(OAc)$_2$/phenanthroline@Zif-8 chemical encaps.

| Wavenumber (cm$^{-1}$) | Peak Intensity | Baseline Intensity | %Intensity increase from Basolite Z1200 |
|---|---|---|---|
| 995.235 | 0.083 | -0.008 | 31.86 |
| 1091.672 | 0.006 | -0.010 | 75.00 |
| 1145.677 | 0.234 | -0.007 | 29.88 | phenanthroline@Zif-8 chemical encaps.

| Wavenumber (cm$^{-1}$) | Peak Intensity | Baseline Intensity | %Intensity increase from Basolite Z1200 |
|---|---|---|---|
| 995.235 | 0.056 | -0.010 | 6.06 |
| 1091.672 | 0.002 | -0.012 | 71.43 |
| 1145.677 | 0.168 | -0.009 | 4.52 | phenanthroline@Zif-8 ball milled

| Wavenumber (cm$^{-1}$) | Peak Intensity | Baseline Intensity | %Intensity increase from Basolite Z1200 |
|---|---|---|---|
| 995.235 | 0.045 | -0.033 | 20.51 |
| 1091.672 | -0.033 | -0.040 | 42.86 |
| 1145.677 | 0.181 | -0.039 | 23.18 |

Proposed that precursor-containing products' increase in peak intensity at 1091.672cm$^{-1}$ relative to Zif-8 is due to presence of phenanthroline in MOF pores (this stretch aligns with stretch in phenanthroline fingerprint region)

*FIG. 14*

| Sample Name | $\lambda_{max}$ (nm) | A | %wt phen |
|---|---|---|---|
| Phen | 287 | 0.114-1.467 | N/A |
| Basolite® Xz1200 | 203 | 0.044 | 0 |
| Phen/Fe@Z8BM | 288 | 0.831 | 10.63 |
| Phen/Fe@Z8EC | 286 | 0.274 | 4.26 |

FIG. 15

| Sample | Signal (AU) | [Fe] ppm | Wt% Fe |
|---|---|---|---|
| Phen/Fe@Z8EC | 0.015 | 3.2 | 0.09 |
| Phen/Fe@Z8BM | 0.011 | 2.0 | 0.04 |
| Basolite® Xz1200 | 0.001 | <0.3 | - |

FIG. 16

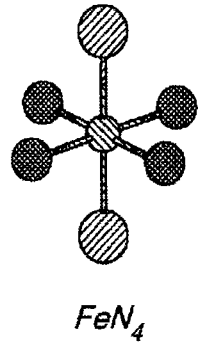
FeN₄
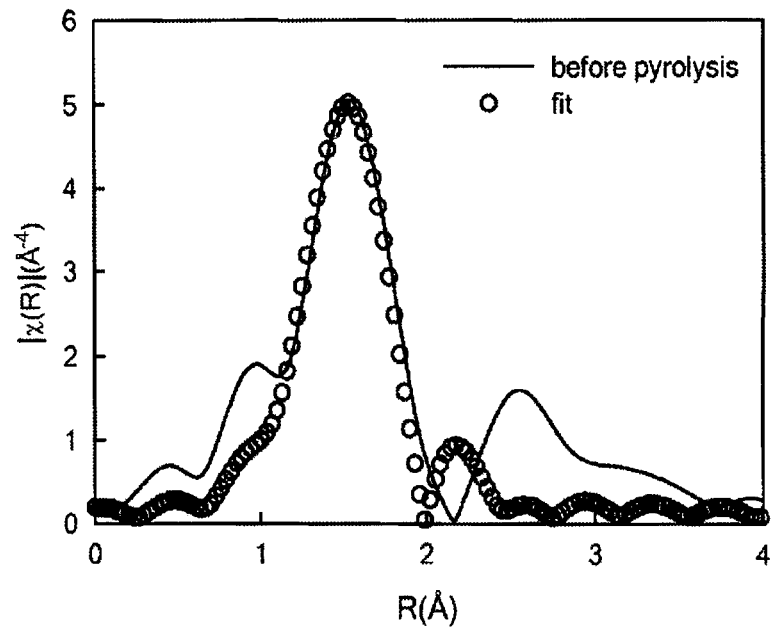
FIG. 24C

| FS fitting | FeN/O_CN | Fe-N R(Å) |
|---|---|---|
| Non-pyrolyzed | 6.5±1.1 | 2.04±0.02 |
| 950HT 0.3V | 4.2±0.5 | 2.08±0.02 |
| 950HT 0.9V | 4.9±0.8 | 2.05±0.02 |

NON-NOBLE METAL ELECTROCATALYSTS FOR OXYGEN DEPOLARIZED CATHODES AND THEIR USES

CROSS-REFERENCE TO RELATED APPLICATIONS

This application claims the priority of U.S. Provisional Applications No. 61/749,650 filed Jan. 7, 2013, entitled "NON-NOBLE METAL BASED ODC CATHODES FOR ODC CATHODES FOR CHLORINE EVOLUTION PROCESS", No. 61/750,118 filed Jan. 8, 2013, No. 61/767,957 filed Feb. 22, 2013, each entitled "NON-NOBLE METAL BASED ODC CATHODES FOR CHLORINE EVOLUTION PROCESS", and No. 61/844,571 filed Jul. 10, 2013, entitled EXPEDITED SYNTHETIC PATHWAYS TO NON-PLATINUM GROUP ELECTROCATALYSTS FOR OXYGEN REDUCTION REACTION FOR ENERGY CONVERSION, STORAGE, AND ELECTROLYSIS, which are hereby incorporated herein by reference in their entireties.

STATEMENT REGARDING FEDERALLY SPONSORED RESEARCH OR DEVELOPMENT

This invention was made with government support under Department of Energy (DOE) Grant Number DE-EE0000459 and Army Research Office (MURI) Grant Number W911NF-09-0227. The government has certain rights in the invention.

BACKGROUND

Use of "depolarizers" in electrolytic reactions helps lower input electrical energy in electrochemical processes. For example, in batteries depolarizers help prevent buildup of hydrogen gas bubbles thereby preventing the voltage, and thereby current, from being reduced. Among the known depolarizers, including sulfur dioxide which is used for lowering energy use in production of hydrogen, oxygen consuming cathodes have gained in importance due to the high onset potential of the oxygen reduction reaction (ORR). Oxygen depolarized cathodes are used in electrolytic production of chlorine from brine solution, and in its recovery from hydrochloric acid, a byproduct of various chemical processes, e.g., production of polymers notably polyvinyl chloride, polyurethanes and polycarbonate, chloroaromatics, and many other components. However, electrochemical chlorine production is currently one of the most energy-intensive processes in the chemical industry, Manufacture of chlorine using oxygen depolarized cathode (ODC) promises to reduce power consumption by as much as 30% compared to standard membrane technology, and is also accompanied with a cut in indirect carbon dioxide emissions. The process integrates use of oxygen with the reaction taking place at the cathode in the manufacture of chlorine by electrolysis of sodium chloride or HCl to produce water instead of hydrogen gas. Oxygen is pumped into the cathode compartment, which reacts with hydrogen to produce water, and the voltage needed for the electrolysis process is reduced by approximately a third. Thus, feeding of gaseous oxygen enables electrolysis to be performed at a lower voltage.

In this process, the conventional cathodic reduction of protons to $H_2$ (g):

$$2H^+ + 2e^- \leftrightarrow H_2(g) \quad E = 0.00 \text{ V vs. RHE} \tag{1}$$

is replaced with the Oxygen Reduction Reaction (ORR):

$$O_2(g) + 4H^+ + 4e^- \leftrightarrow 2H_2O(l) \quad E = 1.23 \text{ V} \tag{2}$$

Thus, overall process is the following:

$$2HCl + \tfrac{1}{2}O_2 \leftrightarrow Cl_2(g) + H_2O(l) \quad E = -0.13 \text{ V} \tag{3}$$

as compared to conventional:

$$2HCl \leftrightarrow 2H_2(g) + 2Cl_2(g) \quad E = -1.36 \text{ V} \tag{4}$$

with a theoretical energy savings of ~700 kWh per ton of $Cl_2$ (g). Thus, the much lower ORR overpotential associated with oxygen consuming gas diffusion electrode (GDE) is expected to result in significant cost and energy savings.

Operation of an electrolytic cell for chlorine production involves use of aqueous solution of hydrochloric acid at concentration as high as 20% (~5 M) and temperature as high as 60° C., which creates a highly corrosive environment. The presence of anions (chloride ions) in such corrosive environment causes poisoning of the catalyst, thereby reducing the efficiency of the cell. Therefore, there is a need to develop ORR catalysts that can resist anion poisoning.

The oxygen reduction reaction (ORR) is one of the most studied reactions in energy conversion systems due to the large overpotential caused by the slow kinetics. Due to the lower proton conductivity and permeability of oxygen in the phosphoric acid environment, high loadings of metal are required. Traditionally platinum based electrocatalyst have been used to facilitate ORR in acidic media, but the scarcity of these materials significantly increases the cost of the system. In addition to the economic disadvantage of platinum based electrocatalyst, there is also the issue of poisoning of these materials by the adsorption of the dihydrogen phosphate anion. The number of electrons transferred per active site of Pt per second is diminished by approximately 70% in the presence of moderate concentrations of phosphoric acid. Phosphoric acid fuel cells (PAFC) are successfully commercialized and presently operate at 80% combined heat and power efficiency, but the cathode materials suffer poisoning effects from the dihydrogen phosphate ion adsorption ($H_2O_4^-$) limiting the performance. Anion adsorption is structure dependent and it has been shown that some Pt-alloys exhibit a heightened tolerance to phosphate poisoning (He, Q. PhysChemChemPhys. 2010. 12, 12544) but cost is still an issue. However, non-platinum group metal catalysts (NPMC) for ORR containing Fe and/or Co have been investigated and progress has been made in developing synthetic strategy for preparing these NPMC have now made these materials viable contenders with Pt-based catalysts for use in acid based systems. (Jaouen, F. et al., 2011)

Current state of the art catalyst for ODC is rhodium based chalcogenite ($Rh_xS_y$/C), currently produced by DeNora. The $Rh_xS_y$/C catalyst outperforms the extremely ORR active carbon supported platinum (Pt/C) catalysts in resisting anion poisoning. The Pt/C catalyst is easily poisoned by chloride ions. Despite a lower activity for oxygen reduction relative to state of the art Pt-based electrocatalysts in most systems, $Rh_xS_y$ is not severely depolarized by contaminants such as chloride ions and assorted organics. However, Rh is a precious metal and the cost of $Rh_xS_y$/C is a drawback for successful commercialization of $Rh_xS_y$/C.

Anion poisoning, which is a common problem in electrocatalysis in aqueous media, is a result of strong interaction of catalytic metal nanoparticles (Pt, Rh, Ru, etc.) with impurities at potentials above potential of zero charge (PZC). The poisoning blocks access of the reactants (e.g., oxygen in ORR reactions) to the active centers on the metal surface, resulting in increased overpotential. Chemisorption of any species, e.g., anions, on the metal surface depends on the free energy of adsorption and free energy of solvation of that species. In acidic environment water molecules act as weak anionic species and interact with the metallic surface through the oxygen atoms of hydroxide ions. More electronegative moieties such as chloride or bromide ions, or other anions when present replace the hydroxide ions. The metal-anion interaction grows in strength with increased positive potentials, which is specifically challenging for oxygen reduction reactions as the ORR onset is desired to occur at high potentials. As shown for adsorption of chloride anions on platinum nanoparticles (FIG. 1) even small concentrations of anions result in significant losses in the activity of the catalyst.

Most reported nonplatinum group metal (non-pgm) catalysts consist of biomimetic $Fe-N_x$ centers which are frequently wrapped within protective graphene layers, and contain non-coordinated metal nanoparticles ($Fe_{NPs}$). The overall catalytic performance and stability of these materials depends upon the structure and distribution of the metal centers throughout the catalyst surface. While the better performing MNC catalyst in this group exhibit promising durability in standard fuel cell environment, most of the protected Fe-consisting nanoparticles are susceptible to oxidation by strong anions like a chloride ion, especially at high concentrations, as in case of catastrophic cathode flooding with concentrated hydrochloric acid in chlorine recovery HCl electrolyzers.

SUMMARY OF THE INVENTION

Methods of synthesizing highly anion resistant non-noble metal electrocatalysts suitable for catalyzing oxygen reduction reaction (ORR) are provided, as are the electrocatalysts resulting from such synthesis.

An aspect of the invention is a method of synthesizing an electrocatalyst for an oxygen reduction reaction, the method including the steps of: (a) reacting an organic ligand, a first transition metal or salt thereof, and a first catalytic precursor to form a product, such that the first catalytic precursor is a heteroatom-containing organic molecule, and such that the product includes a metal organic framework (MOF) including the first transition metal; (b) reacting a second catalytic precursor with the product resulting from (a) until a precipitate is formed, such that the second catalytic precursor is a second transition metal or salt thereof, whereby the first and the second catalytic precursors are encapsulated inside the MOF; and (c) isolating the precipitate and subjecting it to pyrolysis, whereby the first transition metal evaporates (i.e., the first transition metal is volatile at the temperature of pyrolysis) yielding the electrocatalyst. In some embodiments of the method, steps (a) and (b) are performed in a single reaction vessel as a "single pot" reaction.

In various embodiments according to the method of synthesis above, the heteroatom-containing organic molecule provides a heteroatom capable of coordinating a transition metal and supporting catalysis of an oxygen reduction reaction. Further, the pyrolysis can be carried out at about 700° C. to about 1100° C. Further, the electrocatalyst can be cross-linked as a result of the pyrolysis in step (c).

In related embodiments the heteroatom-containing organic molecule includes one or more heteroatoms selected from the group consisting of nitrogen, oxygen, and sulfur. Nitrogen is a preferred heteroatom in certain embodiments.

In certain embodiments the first and second transition metals are non-noble transition metals. For example, the non-noble second transition metal can be selected from the group consisting of iron, cobalt, copper, nickel, and chromium. In a preferred embodiment, the second transition metal is iron. For example, the first transition metal can be selected from the group consisting of zinc and molybdenum. In a preferred embodiment, the first transition metal is zinc.

In various embodiments the first and the second transition metals have oxidation states selected from the group consisting of all known oxidation states for the respective transition metal.

In related embodiments the salt of each of the first and the second transition metals is selected from the group consisting of acetate, nitrate, sulfate, phosphate, and chloride.

In various related embodiments of the method the organic ligand is selected from the group consisting of imidazole, methylimidazole, pyridine, pyridine derivatives, pyrimidine, triazole, tetrazole, napthylene, and napthyridine.

In certain embodiments the second transition metal is in the form of nanoparticles or a colloid accommodated within pores of the MOF. Nanoparticles containing or consisting of, or consisting essentially of the second transition metal can be added to the synthesis, whereby they become incorporated into pores of the forming MOF.

In various embodiments of the method, the first catalytic precursor is selected from the group consisting of phenanthroline, porphyrin, imidazole, pyridine, pyrimidine, and triazole.

In related embodiments the electrocatalyst is resistant to anion poisoning when used in an oxygen reduction reaction.

Another aspect of the invention is a method of synthesizing a metal organic framework (MOF), the method including the steps of: (a) providing a solution including an organic ligand, a first transition metal or a salt thereof, and a first solvent; (b) heating the solution using microwaves, and stirring, whereby a precipitate is obtained; and (c) washing the precipitate with a second solvent thereby obtaining the MOF. For example, the first solvent is selected from the group consisting of dimethylformamide, tetrahydrofuran, diethyl ether, dimethylsulfoxide, and methanol. For example, the organic ligand is selected from the group consisting of imidazole, methylimidazole, pyridine, pyridine derivatives, pyrimidine, triazole, tetrazole, napthylene, and napthyridine. For example, the salt of the first transition metal includes a counterion selected from the group consisting of acetate, nitrate, sulfate, phosphate, and chloride.

In various embodiments the first transition metal has an oxidation state selected from all known oxidation states of the metal.

Further, an aspect of the invention is an electrocatalyst produced according to a method including any one of the preceding methods. In certain embodiments the electrocatalyst further includes nanoparticles, the nanoparticles including or consisting of a non-oxidated metal (M) surrounded with a layer of metal oxide ($M_xO_y$).

Another aspect of the invention is an electrocatalyst including a metal organic framework (MOF) having a graphene-like structure, such that the MOF includes a transition metal coordinated with heteroatoms in the MOF. In certain embodiments the electrocatalyst further includes nanoparticles, the nanoparticles including or consisting of a non-oxidated metal (M) surrounded with a layer of metal oxide ($M_xO_y$).

Another aspect of the invention is a cathode for an electrolytic process for chlorine evolution in a chlor-alkali electrolysis cell, the cathode including the electrocatalyst according to methods above.

Aspects of the invention include a cathode for an electrolytic process for chlorine evolution in an HCl electrolyzer, the cathode including the electrocatalyst according to methods above.

Further included as an aspect of the invention is a cathode for a phosphoric acid fuel cell including the electrocatalyst according to methods above.

In related embodiments the cathode is resistant to anion poisoning. For example, the cathode is resistant to poisoning by dihydrogen phosphate ion.

Another aspect of the invention is a cathode for carrying out an oxygen reduction reaction in an electrolytic process, the cathode including the electrocatalyst according to methods above, such that the cathode is resistant to anion poisoning. In related embodiments the cathode is resistant to poisoning by chloride ion.

Another aspect of the invention is a method of chlorine evolution, the method including the step of electrolyzing brine in a chlor-alkali electrolysis cell, such that the cathode of the cell includes the electrocatalyst according to methods above.

A further aspect of the invention is a method of chlorine evolution including electrolyzing HCl in an HCl electrolyzer, such that the cathode of the electrolyzer includes the electrocatalyst according to methods above.

Another aspect of the invention is a method for generating electrical energy including using a fuel cell including the electrocatalyst according to methods above.

Still another aspect of the invention is a method of performing an oxygen reduction reaction in an atmosphere of less than 100% oxygen, such as an atmosphere of 90% oxygen and 10% nitrogen. The method uses an electrocatalyst of the present invention.

Another aspect of the invention is an electrocatalyst having a uniform distribution of non-noble metal ions within the catalyst.

BRIEF DESCRIPTION OF THE DRAWINGS

FIG. 14 is a table of relative intensities of infrared peaks of Basolite Z1200© (upper left), phenanthroline/Fe(OAc)$_2$ chemically encapsulated in Zif-8 (upper right); phenanthroline chemically encapsulated in Zif-8 (lower left); and phenanthroline chemically ball milled with Zif-8 (lower right). Increase in peak intensity at 1091.672 cm$^{-1}$ relative to Zif-8 of products containing precursors is due to the presence of phenanthroline in MOF pores (this stretch aligns with stretch in phenanthroline fingerprint region).

FIG. 15 is a table of results of UV-Vis quantification of 1,10-phenanthroline chemically encapsulated in Zif-8 (row 5) compared to 1,10-phenanthroline ball milled with Zif-8 (row 4; Proietti, E. et al., 2011). Basolite standard (row 3), and calibration curve generated from 12.5-100.0 uM 1,10-phenanthroline monohydrate dissolved in 1.0M HCl (row 2) are also shown.

FIG. 16 is a table of results of atomic absorption quantification of iron(II) acetate chemically encapsulated in Zif-8 (row 2) compared to iron(II) acetate ball milled with Zif-8 (row 3; Proietti, E. et al., 2011). Basolite standard is shown in row 4.

FIG. 24A-C show various spectra for the evolution of Fe—N$_x$/Fe$_{NPs}$ active sites. High temperature pyrolysis partially destroys FeN$_x$ and produces protected Fe/Fe$_x$O$_y$. FIG. 24A is a XANES spectra of Fe-edge of a MNC catalyst before and after pyrolysis showing 1 s-3 d transition at 7133 eV fingerprint of an environment of coordination number 6.

FIG. 24B is a set of Fourier transformed EXAFS spectra of the MNC electrocatalyst before and after pyrolysis at 950° C.

FIG. 24C is a Fourier transformed EXAFS spectrum of the MNC electrocatalyst showing the initial structure of Fe-center in comparison to the structure of FeN$_4$Cl$_2$.

FIG. 25A is a set of XANES spectra of Fe-edge of MNC electrocatalyst with increasing voltage, showing an edge shift consistent with the redox potential of about 0.8 V.

FIG. 25B is a square wave voltammetry trace showing the redox potential of the MNC electrocatalyst to be approximately 0.8 V.

FIG. 25C is a set of Fourier transformed EXAFS spectra of Fe-edge of MNC electrocatalyst recorded at different voltages and in an oxygen or argon environment showing absorption corresponding to Fe—N/O and Fe—Fe/—O/—C.

FIG. 25D is a table showing change in coordination number (CN) of Fe as a result of increase in voltage (with pyrolysis). The CN increases from 4 to 5, showing absorption of O(H).

FIG. 26A shows delta μ spectra of $FeN_4/Fe_{NPs}$ collected in-situ on Fe-edge at different voltages ranging from 0.3-1.0 V showing edge shift and oxidation of $Fe^{2+}$ to $Fe^{3+}$.

FIG. 26B is a set of delta μ it spectra comparing theoretical FEFF8 calculation corresponding to Fe—NPs-O and Fe—$N_2$+2C—O, with experimental Δμ.

FIG. 26C is experimentally observed XANES spectrum of $FeN_4/Fe_{NPs}$ MNC catalyst at 0.9V.

FIG. 26D is a theoretical XANES spectrum of $FeN_4/Fe_{NPs}$ MNC catalyst having 10% $Fe_{NPs}$.

FIG. 27A is a set of Fourier transformed EXAFS spectra of M-$N_4$ and $Fe_{NPs}$ sites before and after treatment with $H_2O_2$ for removal of nanoparticles. A dramatic decrease in Fe—Fe absorption is observed upon $H_2O_2$ treatment.

FIG. 27B is a set of current (ring current) measurements showing a decrease in the active sites available following peroxide/Acid treatment (second from top) compared to that before treatment (top curve).

FIG. 27C is a schematic diagram showing that peroxide attacks graphene sheets that protect Fe/$FeO_x$ NPs. (Wu G. et al., 2011).

FIG. 27D is a set of current measurements showing that Fe—$N_4$ is sufficient for both $O_2$ and $H_2O_2$ reduction in alkaline (0.1 M KOH) condition.

FIG. 29A shows spectra based on theoretical FEFF8 calculation for $FeN_4C_{10}$—O, and for FeFe—O.

FIG. 29B shows theoretical spectra for O—$FeN_4$/O—$Fe_{NPs}$ for different percentages of $Fe_{NPs}$.

FIG. 29C shows experimental spectra collected in-situ at different voltages. Experimental data indicate the composition to be about 90% $FeN_4$/10% $Fe_{NPs}$.

DETAILED DESCRIPTION OF THE INVENTION

The invention provides highly anion resistant electrocatalysts suitable for catalyzing an oxygen reduction reaction (ORR). The catalysts contain a transition metal which is a non-noble metal (i.e., non-platinum group metal), carbon, and a heteroatom organized into graphene-like sheets containing the heteroatoms, which coordinate the evenly distributed atoms of the transition metal. As a result of the pyrolysis step used to form the catalyst, the catalyst structure is cross-linked and therefore robust. In various embodiments the catalysts include N as the heteroatom and Fe as the transition metal which form active sites having Fe—$N_4$ stoichiometry ($Fe_xN_yC_z$) as part of a metal organic framework (MOF), or associated with a MOF by incorporation into pores of the MOF. In other embodiments the electrocatalysts further include nanoparticles of Fe ($Fe_{NPs}$) or another transition metal. Applications of the catalysts described herein include preparation of oxygen decoupled cathodes (ODC) for chlorine evolution using, e.g., chlor-alkali cells or HCl electrolyzers; and for use in fuel cells, such as phosphoric acid fuel cells which use phosphoric acid as the membrane electrolyte. Phosphoric acid fuel cells are successfully commercialized and presently operate at 80% combined heat and power efficiency, but the cathode materials suffer poisoning effects from the dihydrogen phosphate ion adsorption ($H_2O_4^-$) limiting the performance. (Shah et al., 2007), which are overcome by the catalysts of the present invention.

The $Fe_xN_yC_z$ active site containing electrocatalysts described here are comparable in performance to state of the art catalysts using noble metals, e.g., Pt/C and $Rh_xS_y/C$, with regard to chlorine evolution (chlor-alkali cells and HCL electrolyzers), or with regard to production of current (fuel cells). The present catalysts are superior to the state of the art catalysts in resisting anion poisoning, e.g., chloride ion poisoning (chlor-alkali cell and HCL electrolyzer), or dihydrogen phosphate ion poisoning (phosphoric acid fuel cells).

Figure 1A:
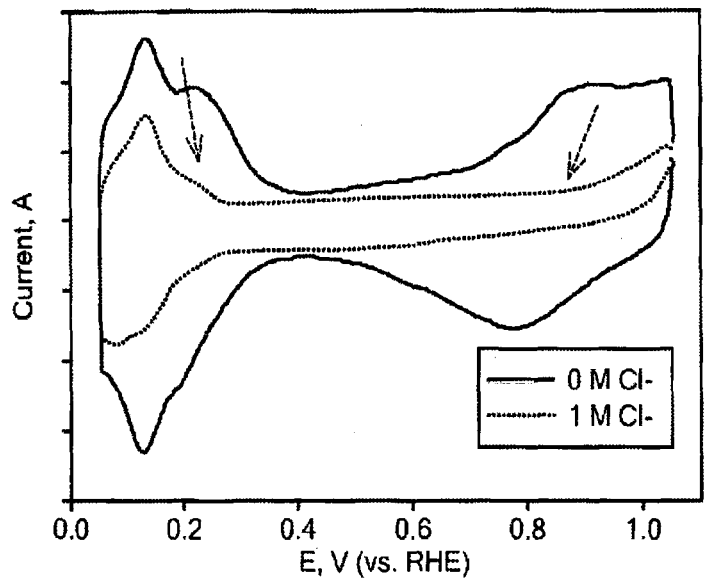
FIG. 1A is a cyclic voltammogram of a carbon supported platinum (Pt/C) rotating disc electrode (RDE), showing the effect of chloride ions (1M) on current produced (y-axis). The voltage sweep is shown in the x-axis. A reversible hydrogen electrode (RHE) was used as a reference electrode.
Figure 1B:
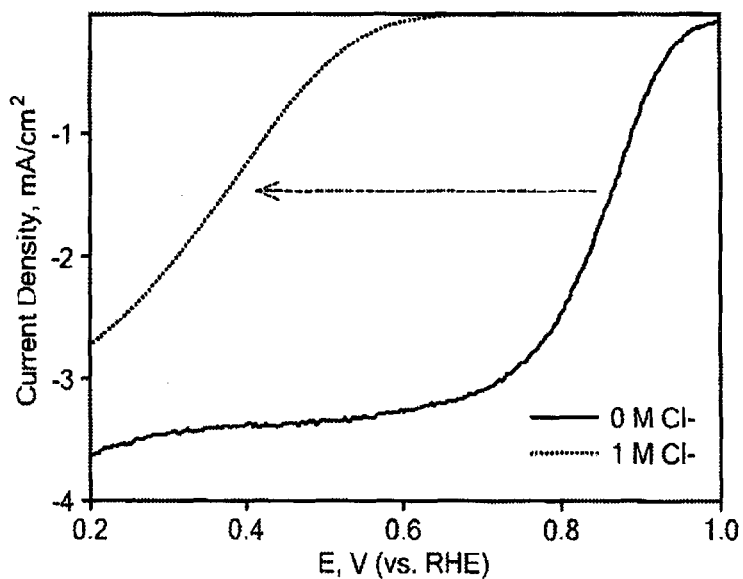
FIG. 1B is a graph showing ORR polarization curves of the Pt/C RDE in the presence of 1M $HClO_4$ (solid line), and in the presence of 1M HCl (dotted line). RDE parameters: 14 g Pt/$cm^2$ glassy carbon (GC; 0.196 $cm^2$).
Figure 2A:
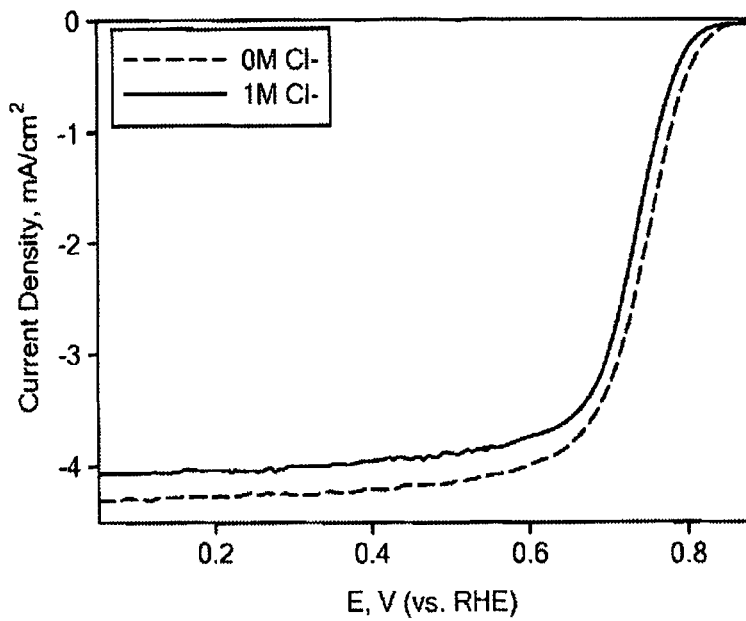
FIG. 2A is a graph of ORR polarization of electrolytic reactions using a RDE with a $Fe_xN_yC_z$ catalyst at 1M HCl (solid line) or at 1M $HClO_4$ (dashed line, no chloride ion) at room temperature. The relevant parameters for the RDE and the polarization measurements are: voltage sweep 10 mV/sec and 900 rpm; 0.6 mg catalyst/$cm^2$ GC (0.196 $cm^2$); reversible hydrogen electrode (RHE), and Carbon cloth counter electrode.
Figure 2B:
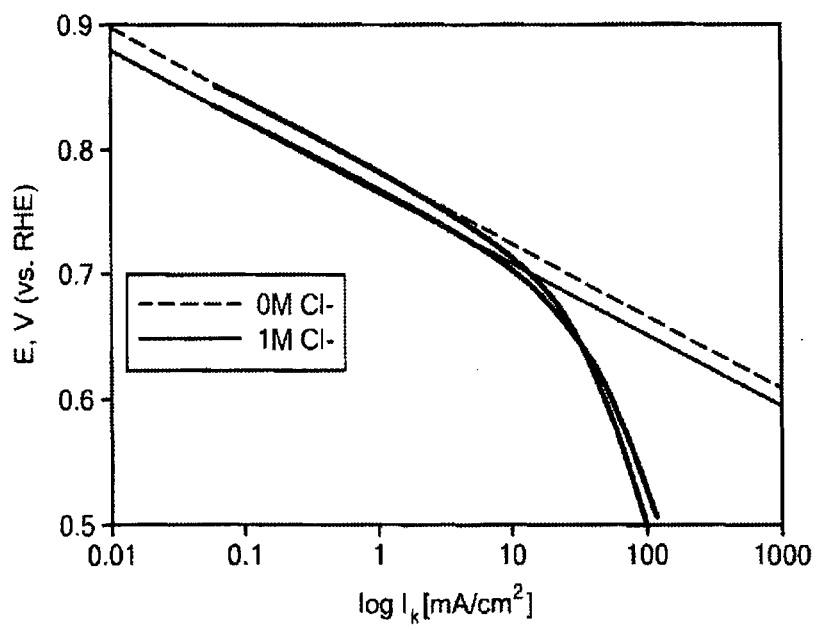
FIG. 2B shows Tafel plots of the electrolytic reactions shown in FIG. 2A.
Figure 2C:
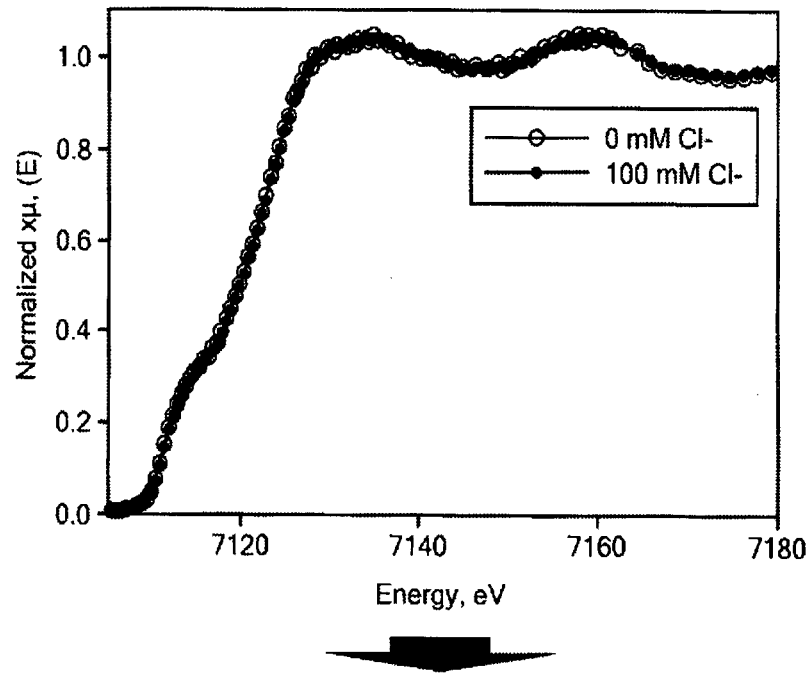
FIGS. 2C and 2D are X-ray Absorption Near Edge Structure (XANES) spectra, and Fourier transformed Extended X-Ray Absorption Fine Structure (EXAFS) spectra respectively, of the $Fe_xN_yC_z$ catalyst used in the electrolysis reactions of FIGS. 2A and 2B collected in-situ on Fe k-edge in 0.1M $HClO_4$ in the absence (black) and presence (grey) of $Cl^-$ ions.
Figure 2D:
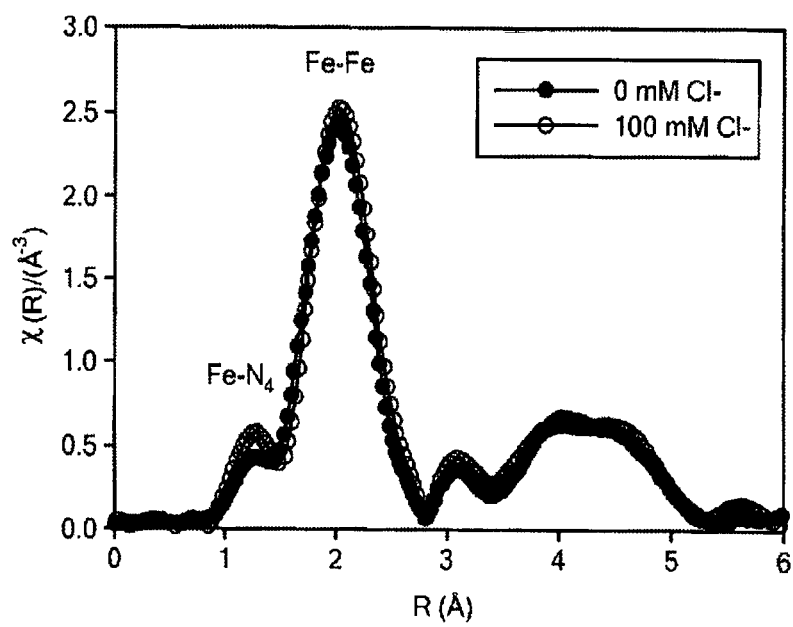
Figure 3A:
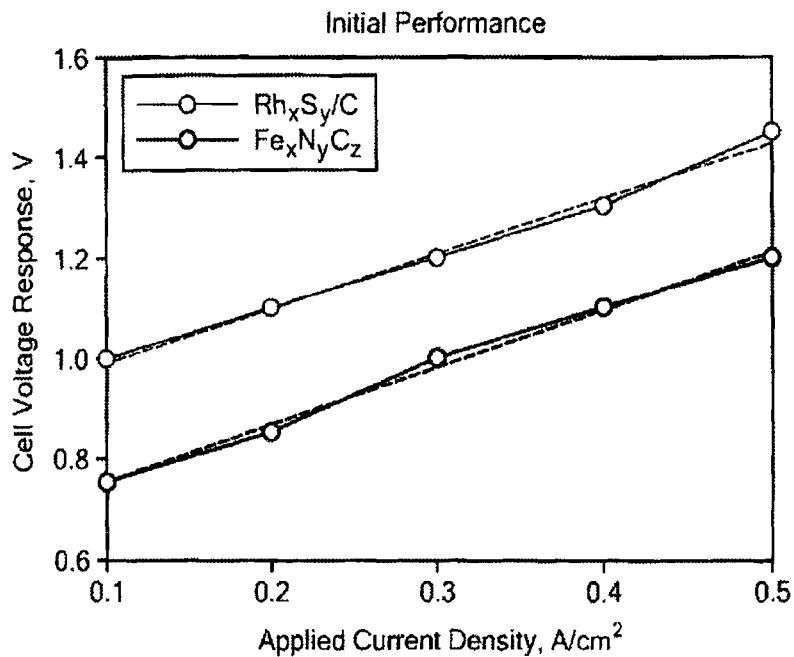
FIG. 3A is a graph of voltage response as a function of applied current density of a HCl cell using either $Rh_xS_y$/C (grey; 1 mg Rh/$cm^2$) or $Fe_xN_yC_z$ (3 mg/$cm^2$) catalyst before simulated shutdown. The solid and broken lines represent presence and absence, respectively, of chloride ions.
Figure 3B:
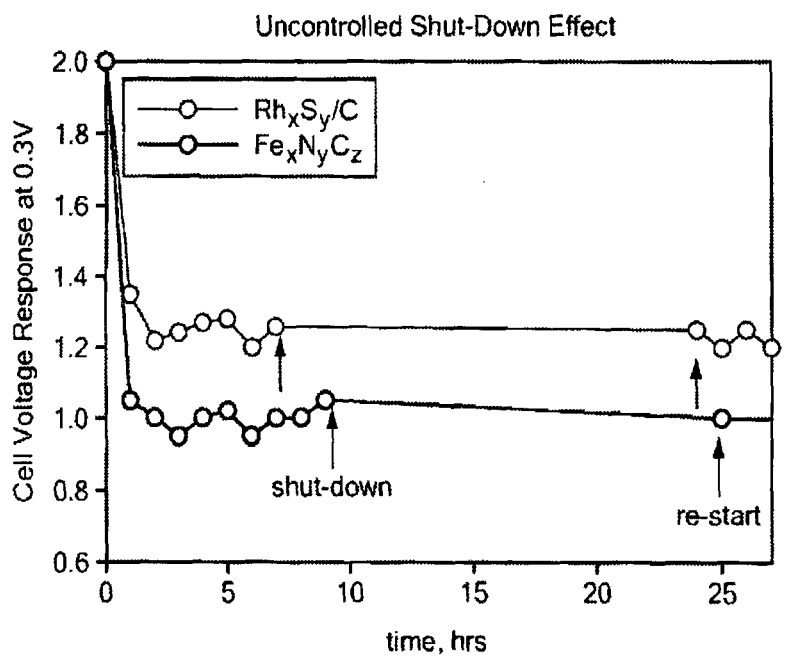
FIG. 3B is a graph of voltage responses at a current density of 0.3 Å/$cm^2$ of a HCl cell as a function of time using either the $Rh_xS_y$/C (grey) or the $Fe_xN_yC_z$ catalyst (FIG. 3A) after simulated shutdown brought about by flooding with hot 5M hydrochloric acid. Anode: 5M HCl/$Cl_2$ @ 55 C, and cathode: $Rh_xS_yC$, 1 mg Rh/$cm^2$ or FeNC 3 mg/$cm^2$, on 6.25 $cm^2$ gas diffusion layer (GDL) and 1 mg/$cm^2$ Nafion. The catalytic ink was made with a 1:1 catalyst-to-Nafion.

The new ODC materials derived from MOF described herein are immune to anion poisoning (FIG. 2), are capable of reducing overall cell voltage below that required for a state of art $Rh_xS_yC$ catalyst, and possess comparable durability, even in case of the catastrophic events such as a power outage (FIG. 3), resulting at least in part from their cross-linked structure. The ORR polarization of electrolytic reactions measured using a RDE with a $Fe_xN_yC_z$ catalyst at 1M HCl (solid line) or at 1M $HClO_4$ (dashed line, no chloride ion) at room temperature is shown in FIG. 2A. Tafel plots of the electrolytic reactions (FIG. 2A) are shown in FIG. 2B, and the effect of chloride anions on ORR activity is summarized in Table 1 below. Table 2 below shows the results of FT fitting of the $Fe_xN_yC_z$ material before and after the simulated shutdown (FIG. 3).

TABLE 1

Summarized effect of chloride anions on ORR activity

| Tafel Slope, mV/dec | | $i_{lim}$, mA/cm$^2$ | | $E_{1/2}$, V | |
|---|---|---|---|---|---|
| 0 mM Cl$^-$ | 1M Cl$^-$ | 0M Cl$^-$ | 1M Cl$^-$ | 0M Cl$^-$ | 1M Cl$^-$ |
| 57 | 57 | 4.3 | 4.05 | 0.75 | 0.74 |

TABLE 2

FT Fitting Results of the Fe$_x$N$_y$C$_z$ material before and after the simulated shutdown

| | Fe—CN | | R, A | |
|---|---|---|---|---|
| | initial | Post shut-down | initial | Post shut-down |
| Fe—C | 1.4+/0.513 | 1.29 | 2.5 | 2.5 |
| Fe—Fe | 7.4(+/−0.809) | 8.2 | 1.99 | 2.09 |

Figure 19A:
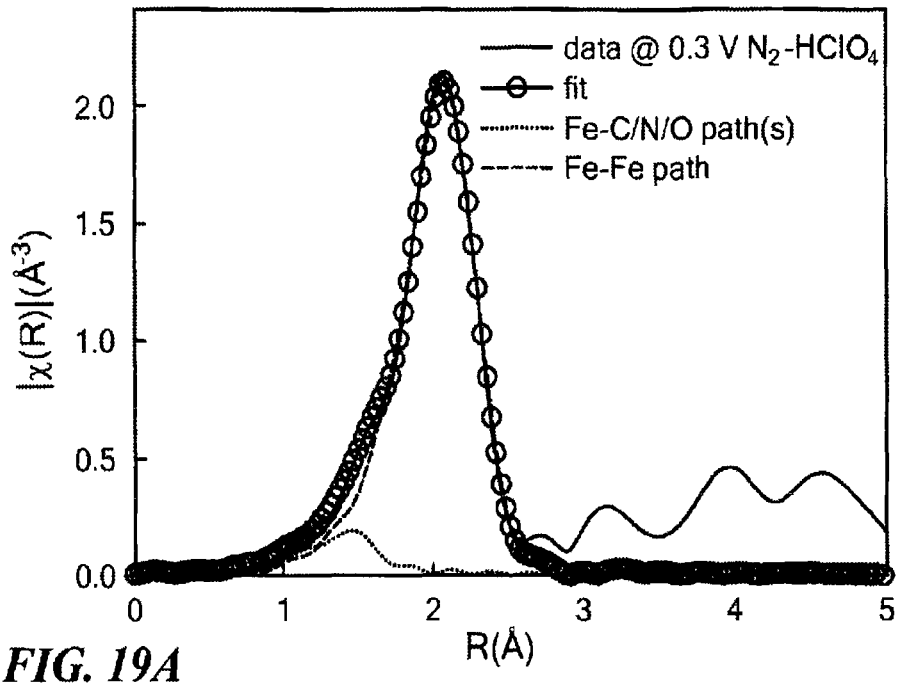
FIG. 19A shows X-ray absorption spectra (XAS), specifically a Fourier transform of EXAFS (extended X-ray absorption fine structure) spectra of encapsulated FeMOF electrocatalyst. The encapsulated FeMOF is mostly comprised of FeNPs, indicated by the Fe—Fe scattering in the Fourier transform plot. A minor contribution (lowermost curve) of a Fe—C/N/O scattering path is also observed.
Figure 19B:
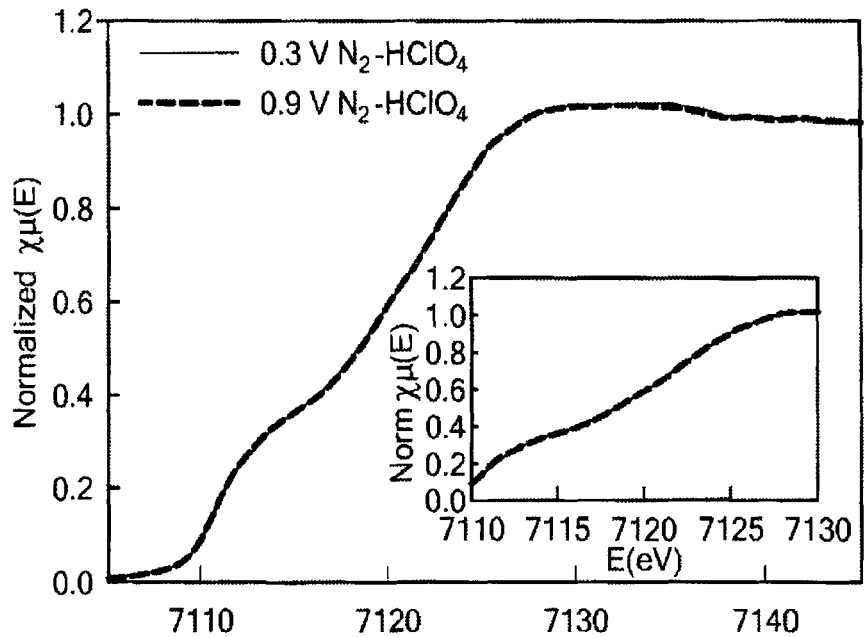
FIG. 19B is a graph showing XANES (x-ray-near-edge-spectrum) plots of encapsulated FeMOF electrocatalyst at two different voltages. No change was observed with increase in voltage.
Figure 20A:
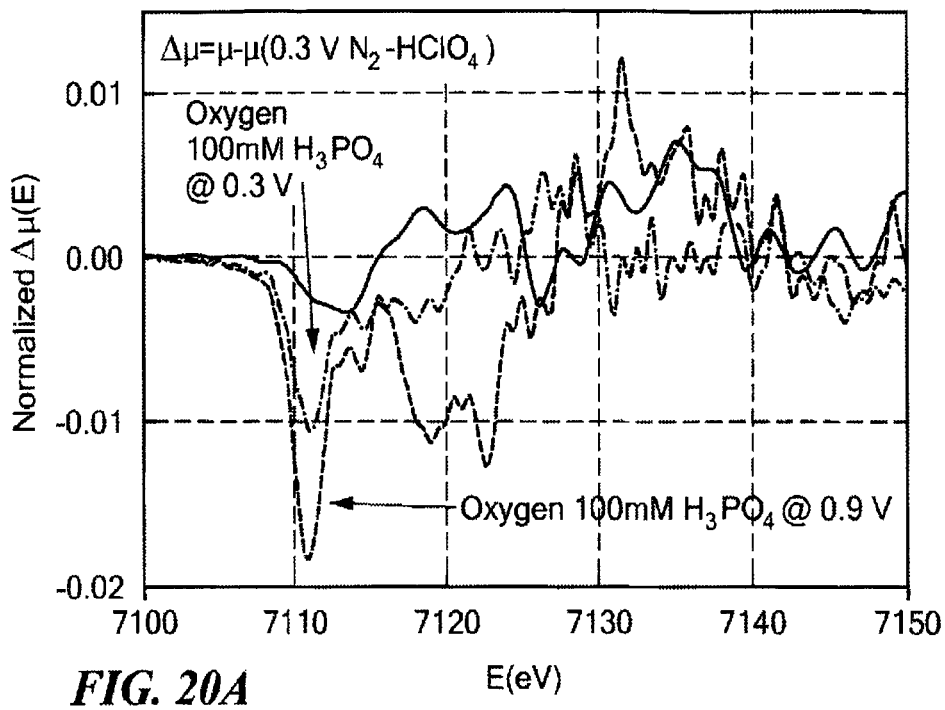
FIG. 20A and FIG. 20B show results of a subtractive method (Delta mu) of investigating adsorbates on the surface of a catalyst. The spectrum of a clean surface is subtracted from the spectrum of a surface with adsorbates in order to identify how the surface of the catalyst is poisoned. Spectrum of the electrocatalyst in an electrolyte known to be free of anions that adsorb on the surface of the electrocatalyst was recorded. Next, 100 mM phosphoric acid, a known poison for the traditional platinum catalyst, was introduced into the electrolyte. Delta Mu (Δμ) plots of FIGS. 20A and 20B showed that dihydrogen phosphate anion adsorbs onto the surface of the encapsulated FeMOF, and that there is an increase in adsorption with increased potential. Comparison of the differences between oxygen saturated and the nitrogen saturated electrolytes show that adsorption is larger in nitrogen suggesting that oxygen molecules are able to displace the dihydrogen phosphate anion, and therefore the active sites of these catalyst are not poisoned.
Figure 20B:
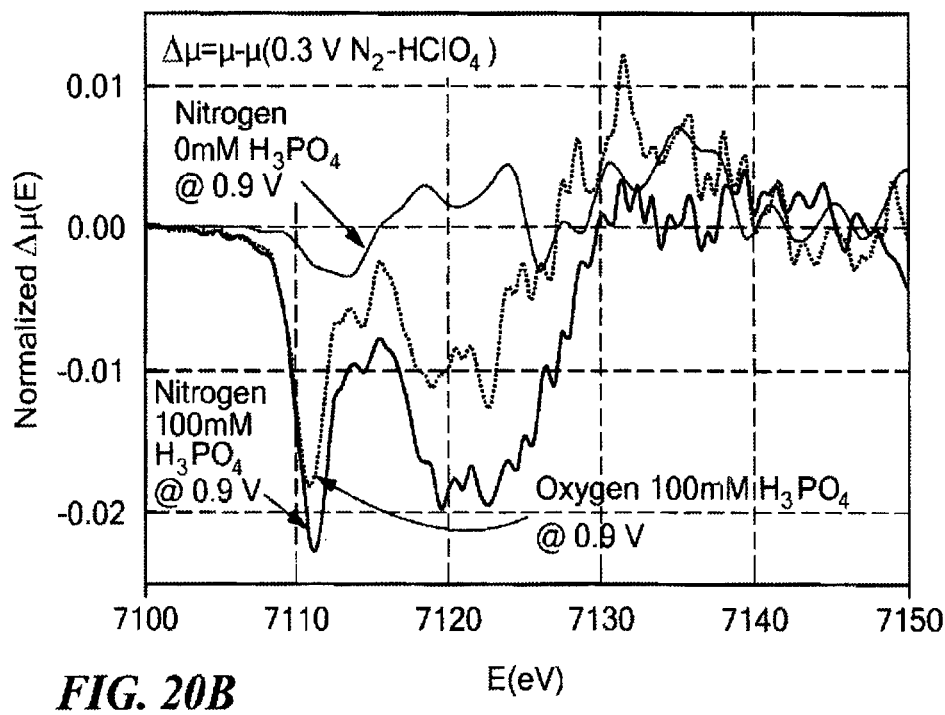
Figure 20C:
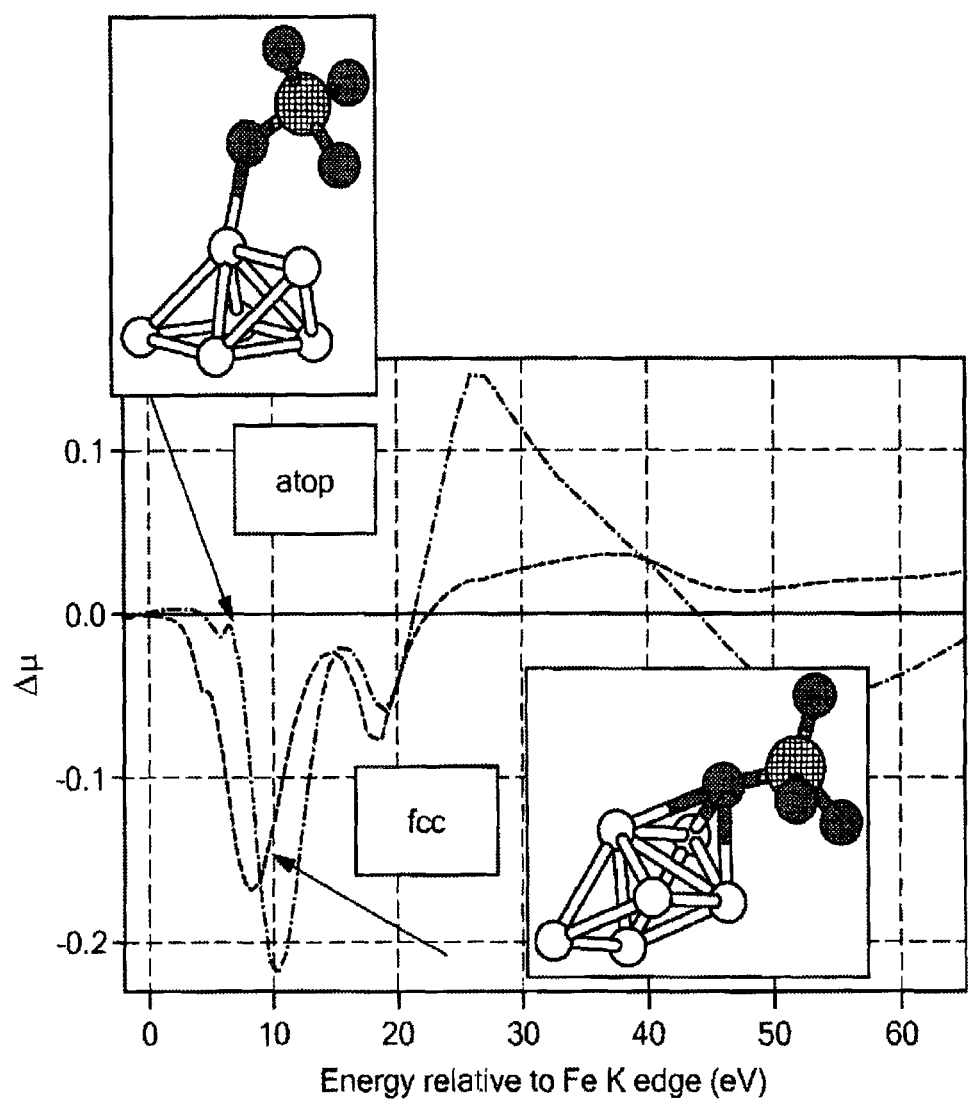
FIG. 20C shows that when experimental line shape of Δμ is compared with that obtained theoretically, dihydrogen phosphate anion is likely adsorbed in an atop mode.
Figure 21A:
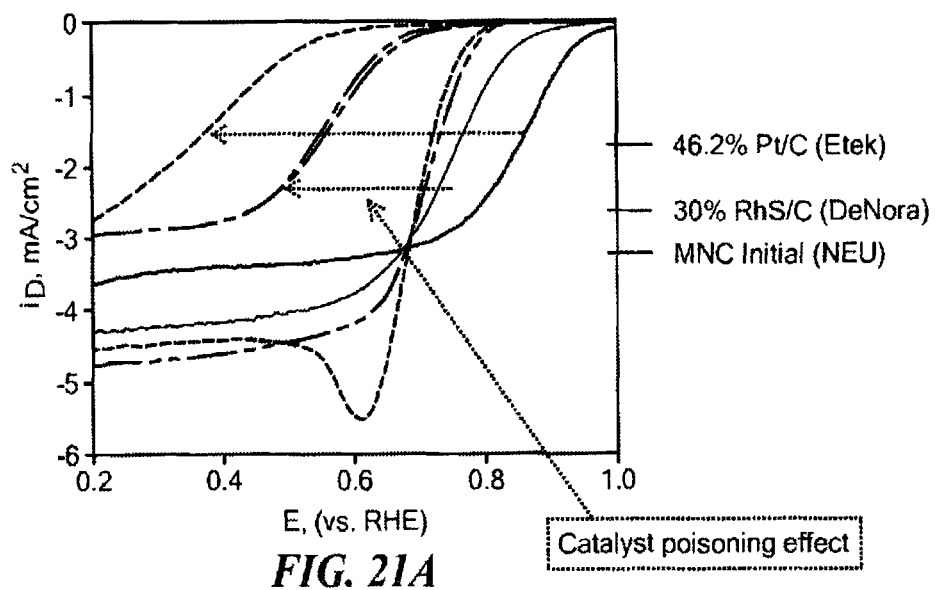
FIG. 21A is a RDE ORR graph (900 rpm) of comparison of chloride ion poisoning of supported Pt (upper horizontal arrow) and Rh-based (lower horizontal arrow) catalysts (0.196 cm$^2$ glassy carbon electrode, Ag/AgCl reference, and C-counter electrode) with that of a MNC catalyst (two curves from the bottom). The broken and solid lines correspond to presence and absence of chloride ions. Catalyst were loaded as follows: MNC: 600 μg/cm$^2$ with about 15 μg/cm$^2$ metal; Rh$_x$S$_y$/C: 16 μg Rh$_x$S/cm$^2$; Pt/C: 14 μg Pt/cm$^2$. MNC catalysts showed superior performance in the presence of poisonous chloride ions. High current densities and low over-potentials are obtained even at high concentrations of chloride ions.
Figure 21B:
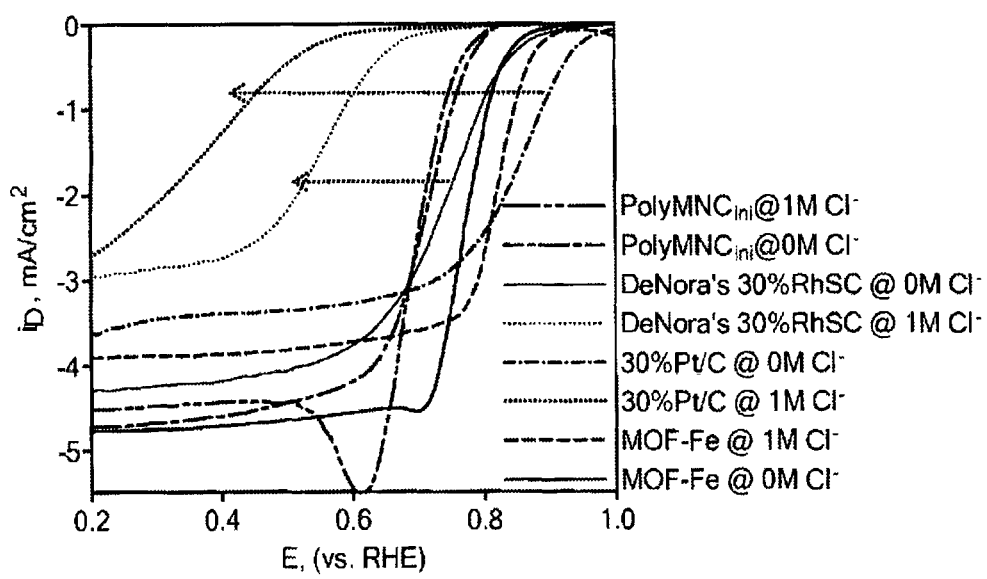
FIG. 21B shows the same comparison as in 21A, except for also comparing poisoning with iron containing metal organic framework, MOF-Fe.
Figure 21C:
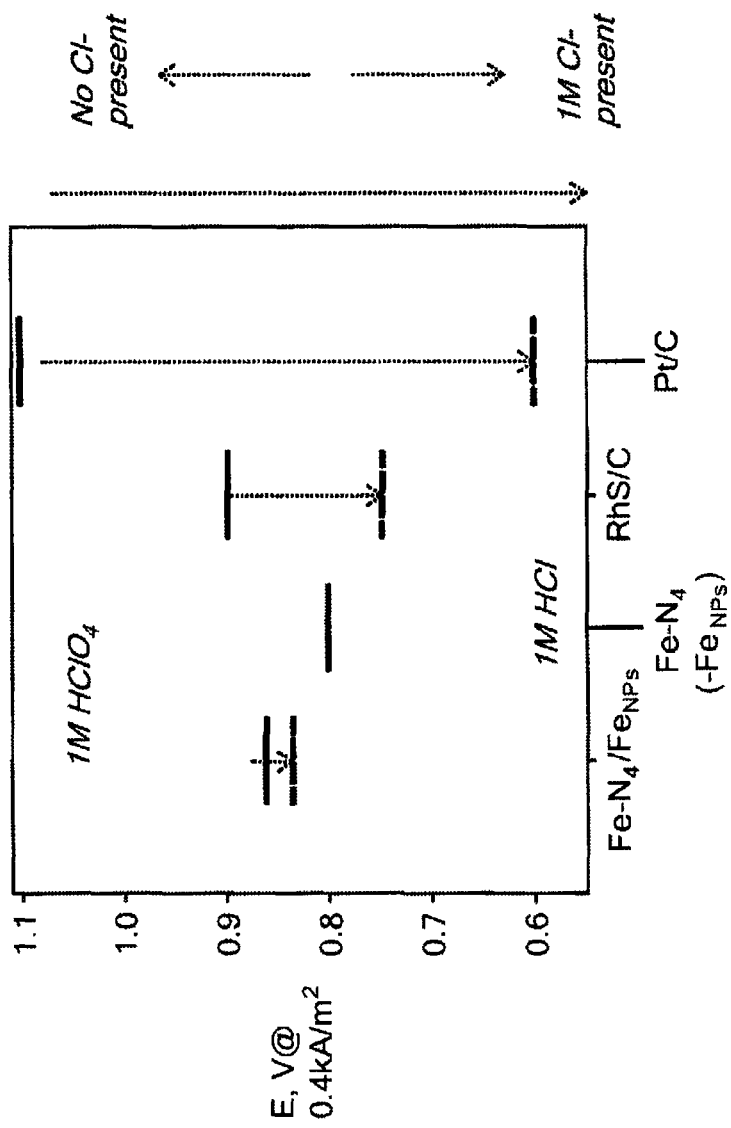
FIG. 21C shows comparison of chloride ion poisoning between MNC catalysts with and without Fe$_{NPs}$, in addition to comparison with chloride ion poisoning of supported Pt and Rh-based catalysts.
Figure 22A:
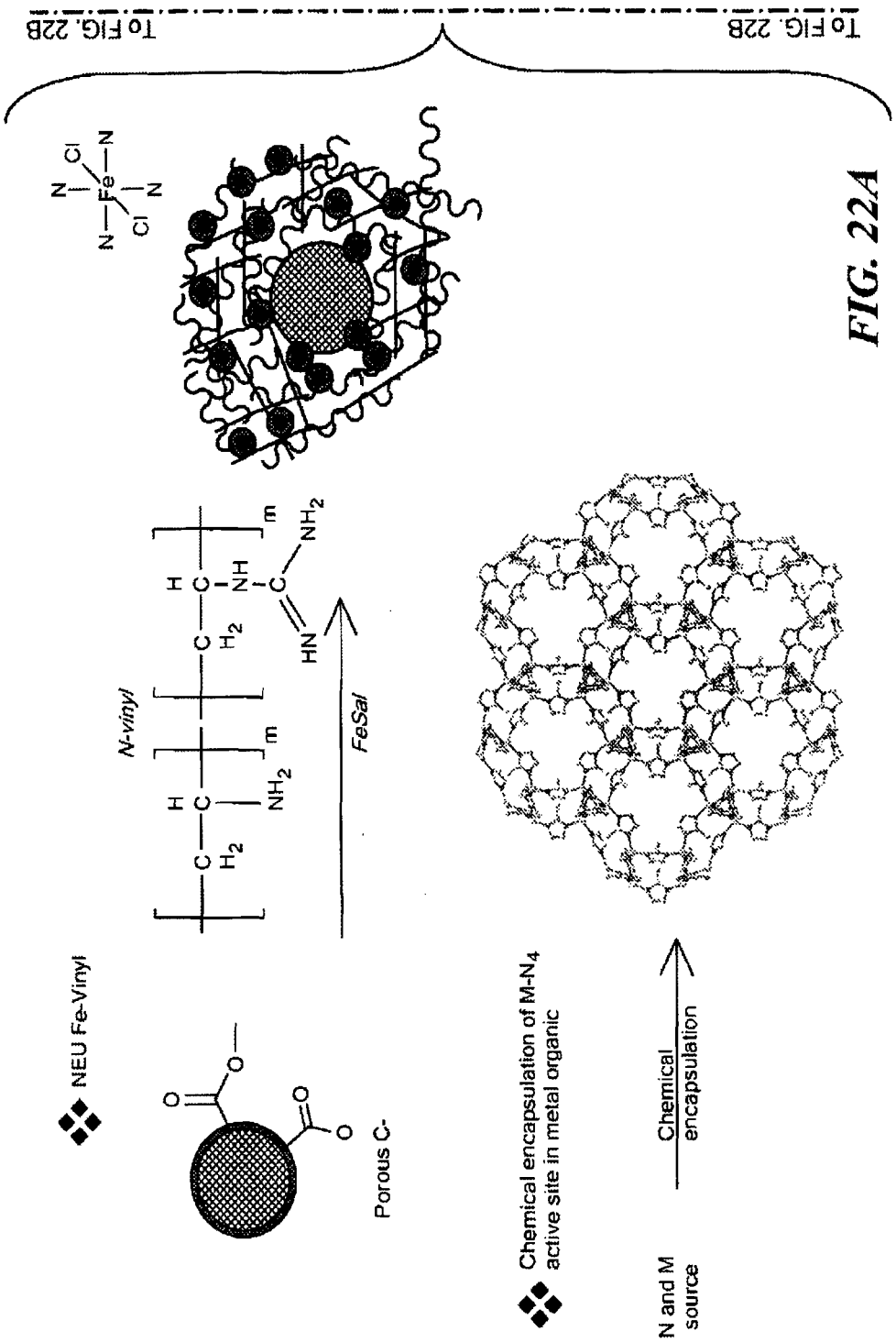
FIG. 22 is a schematic diagram of various synthetic pathways leading to electrocatalysts having two types of active sites, M-N$_4$ and Fe$_{NPs}$.
Figure 22B:
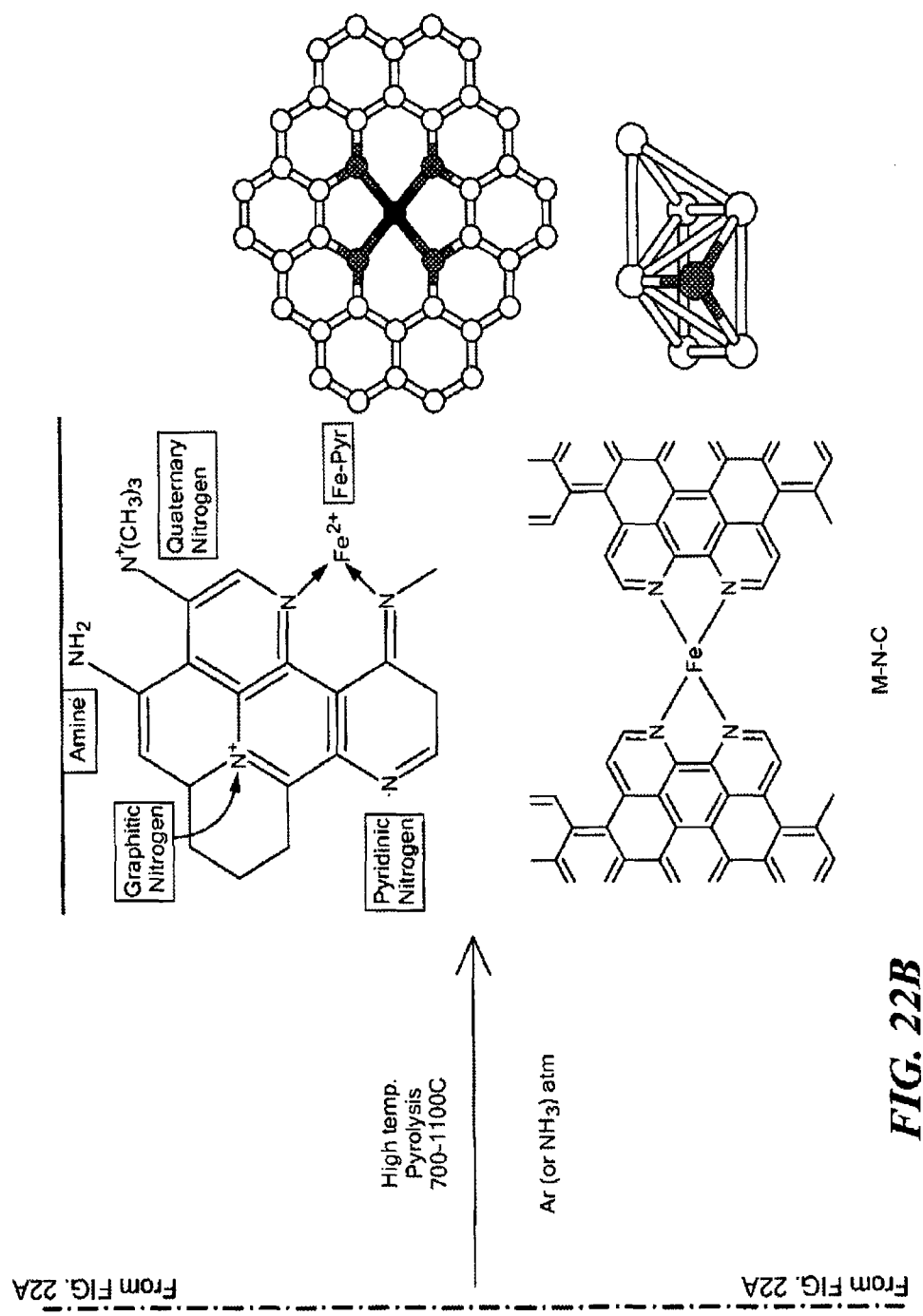
Figure 23A:
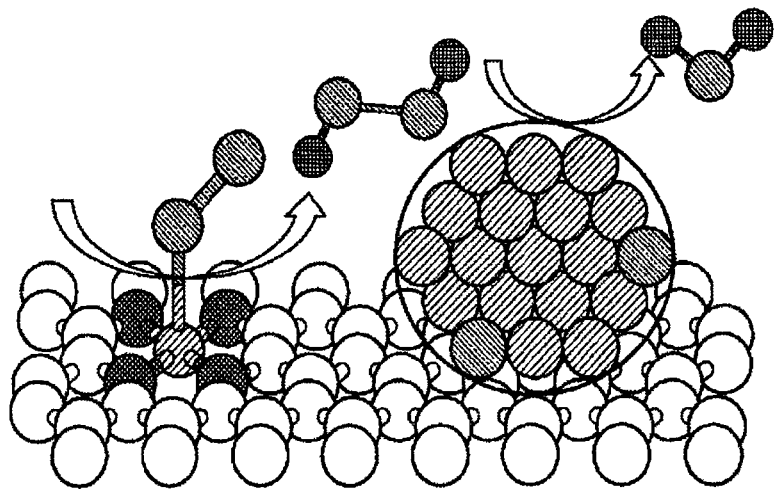
FIG. 23A is a schematic diagram of the Bi-Functional mechanism (Olson T et al., 2010) explaining the role played by the two types of active sites of a non-platinum group (non-PGM) MNC. According to this mechanism the first metal site engages N$_4$/N$_2$ moiety (but may not require transition metal necessarily) and is responsible for oxygen reduction to hydrogen peroxide, which is followed by reduction of hydrogen peroxide to water on the second site (Fe$_{NPs}$ site).
Figure 23B:
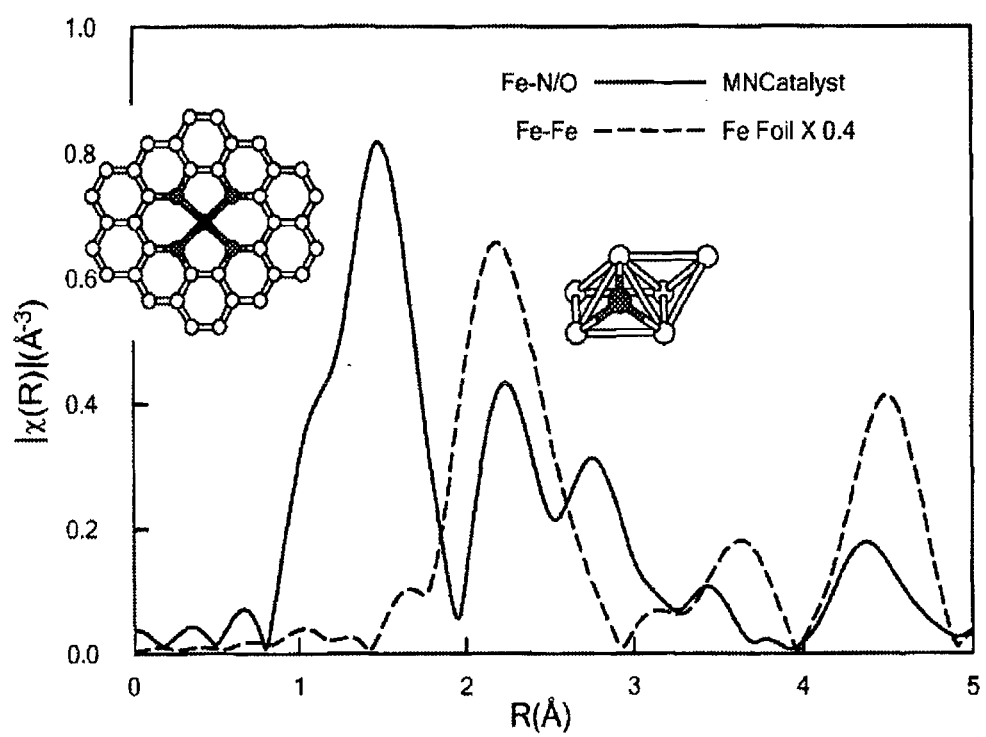
FIG. 23B is a Fourier transformed EXAFS spectrum of MNC catalyst showing Fe—N/O and Fe$_{NPs}$ signatures (solid line) compared to that of a Fe—Fe foil on Fe k-edge collected in-situ in 0.1M HClO$_4$.
Figure 24A:
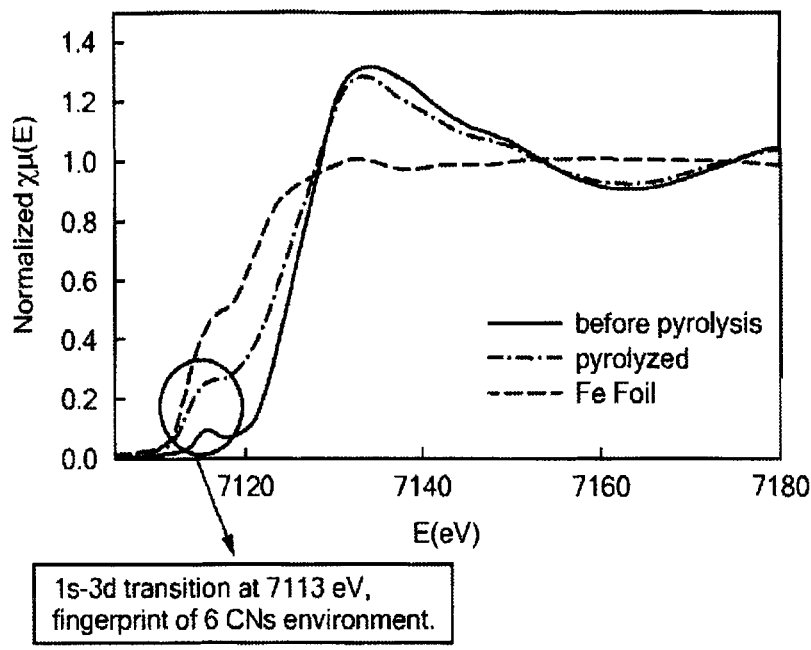
Figure 24B:
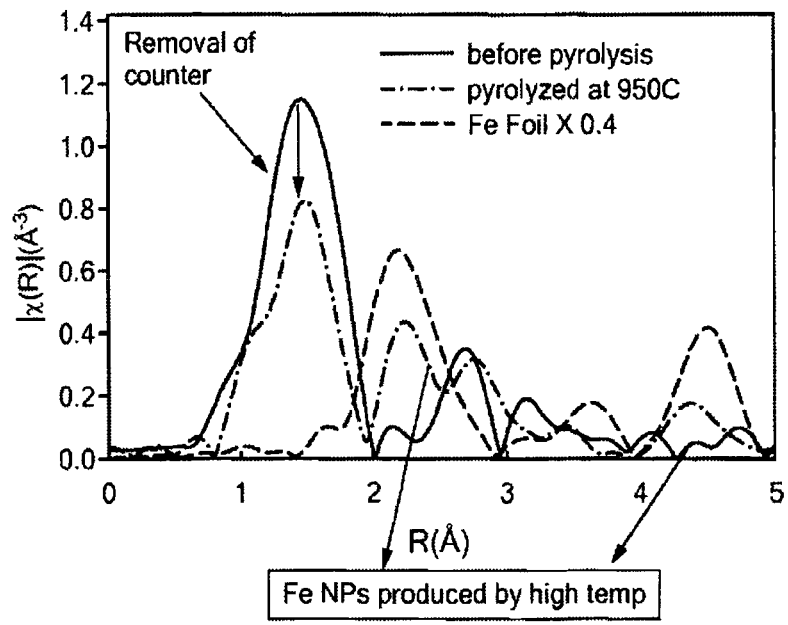
Figure 25A:
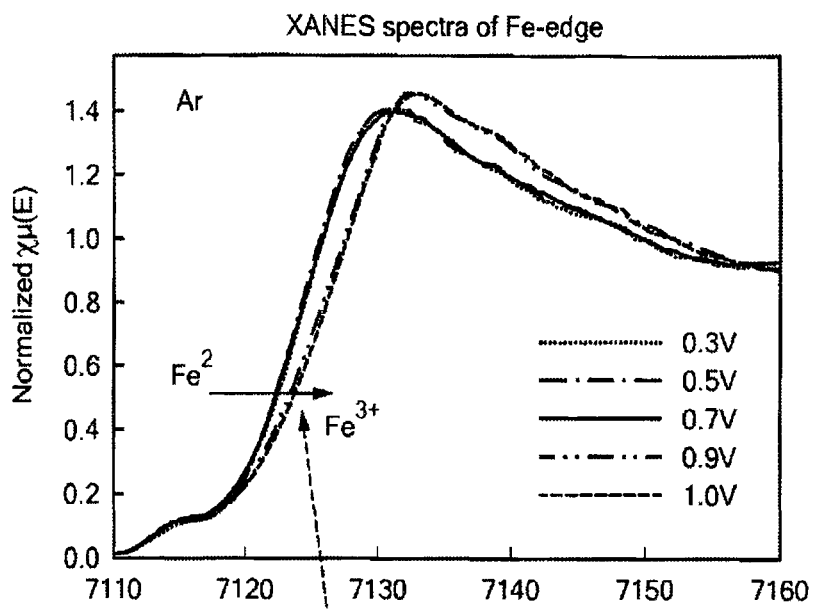
FIG. 25A-D show results in support of Fe$^{2+}$—N$_4$ being the active center.
Figure 25B:
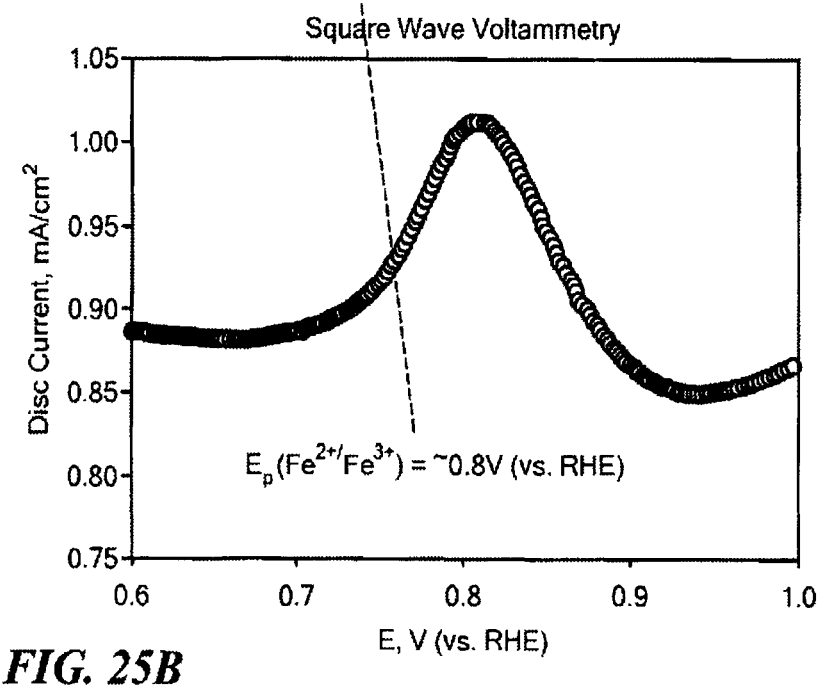
Figures 25C, 25D:
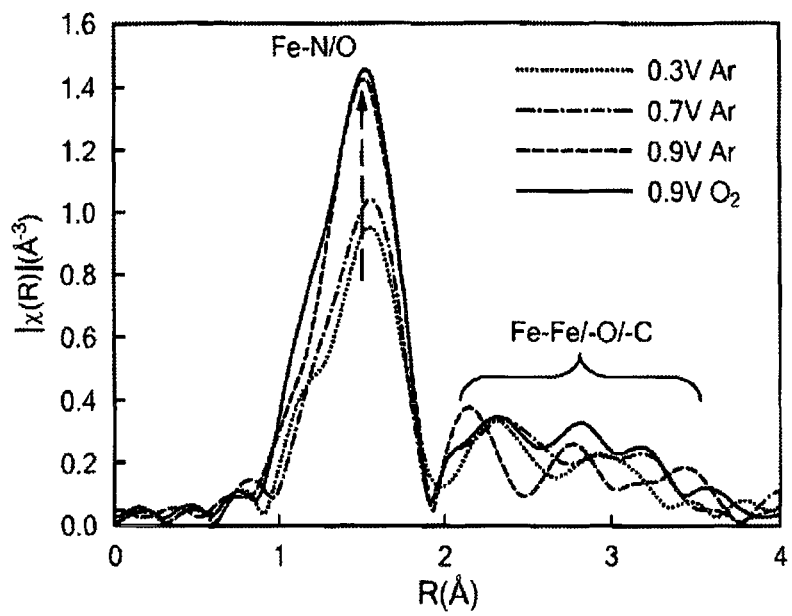
Figure 26A:
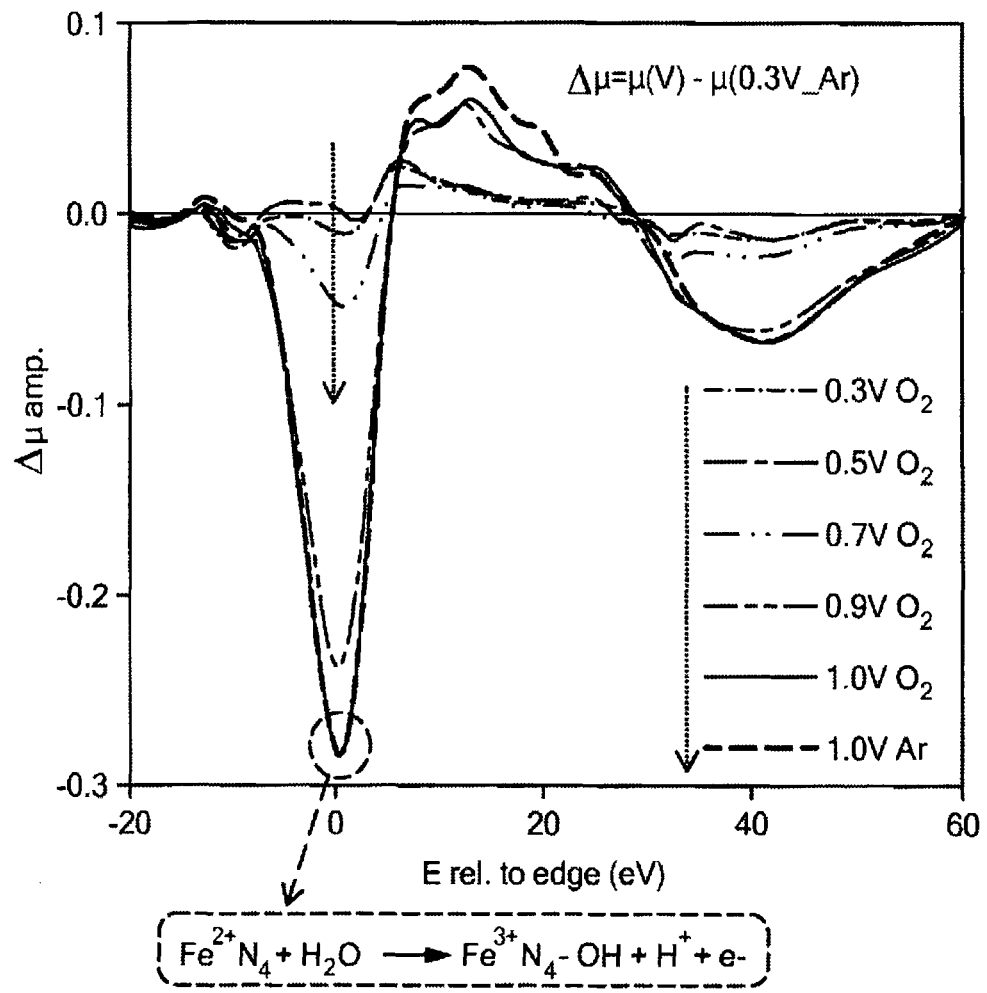
FIG. 26A-D is a set of XAS spectra recorded at in-situ conditions showing a typical behavior of MNC catalysts.
Figure 26B:
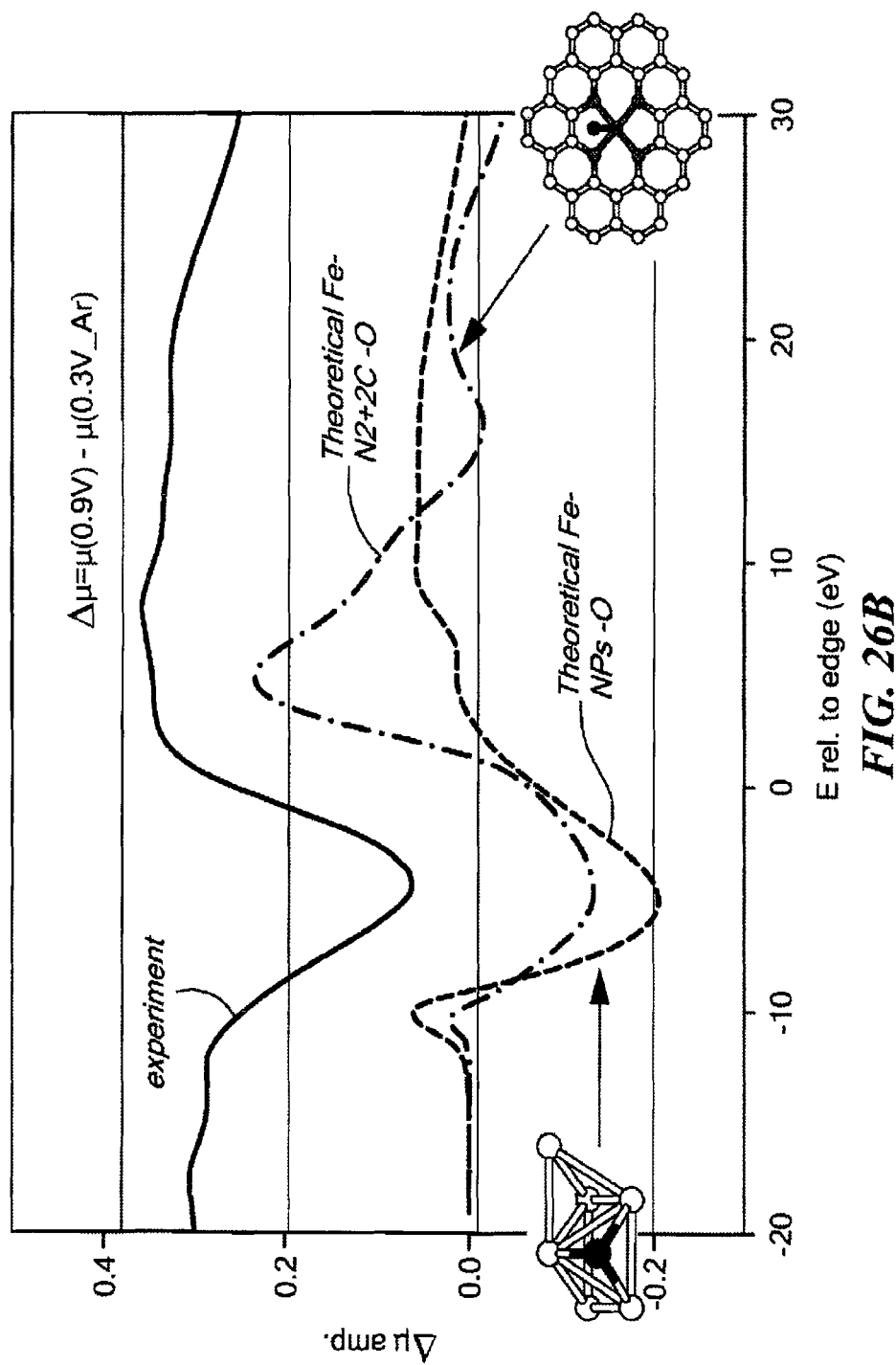
Figure 26C:
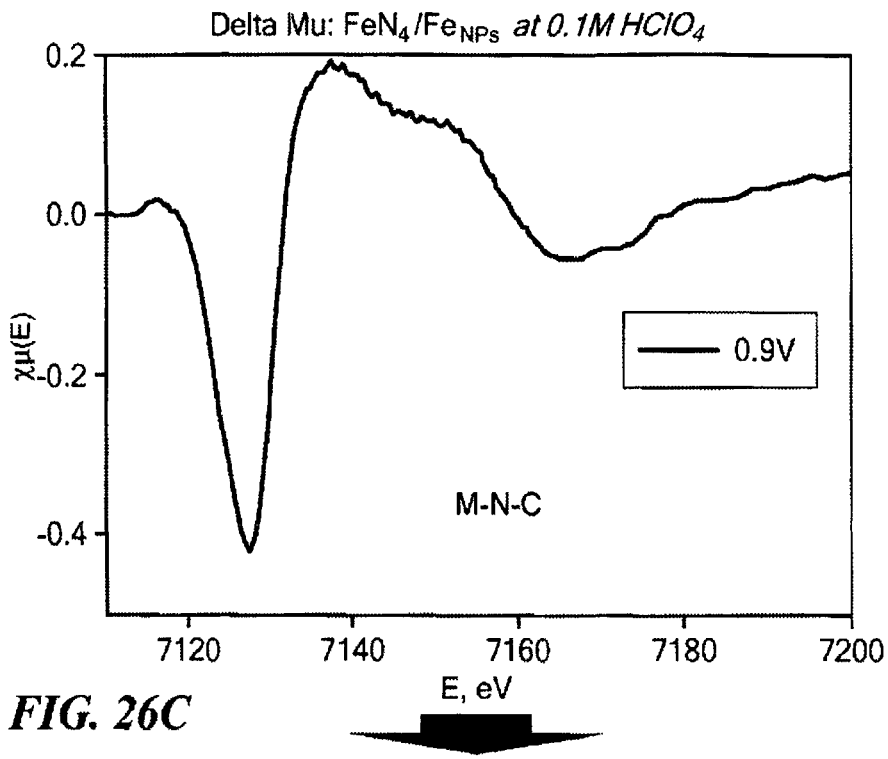
Figure 26D:
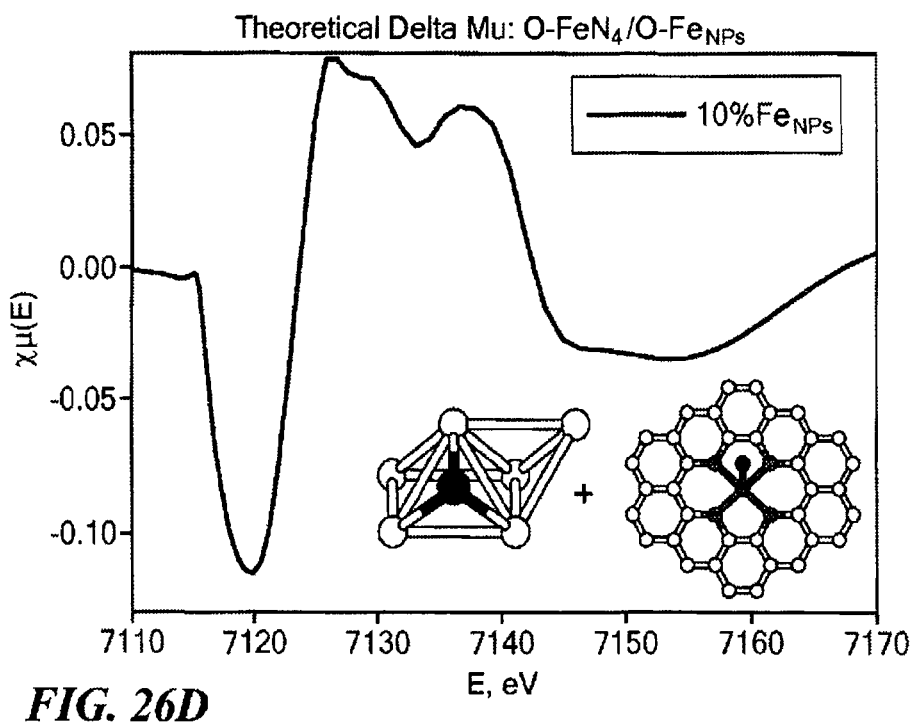
Figure 27A:
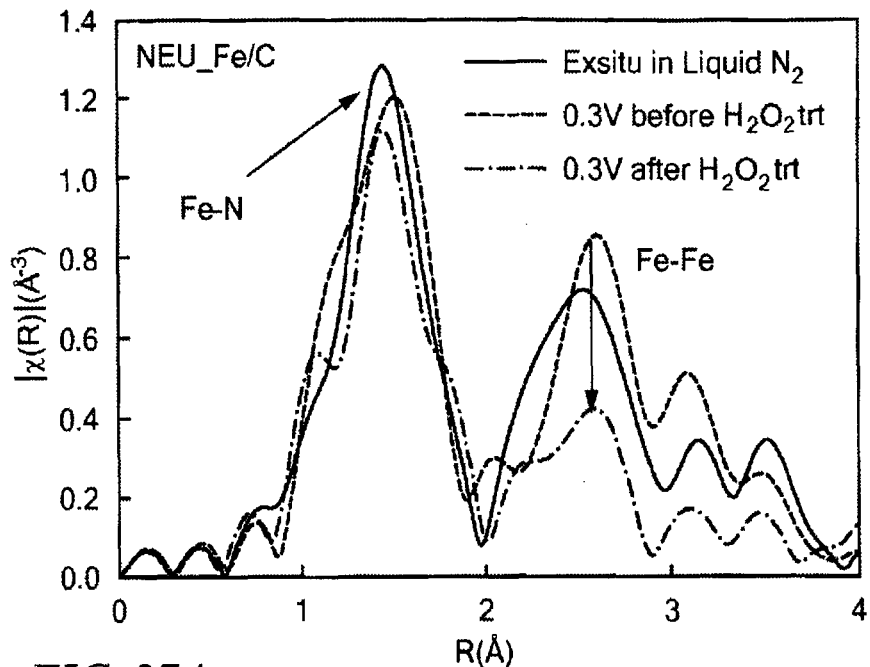
FIG. 27A-D is a set of spectra, current measurements and schematic diagram for observations of M-$N_4$ and $Fe_{NPs}$ sites, and the effect of selective removal of nanoparticles.
Figure 27B:
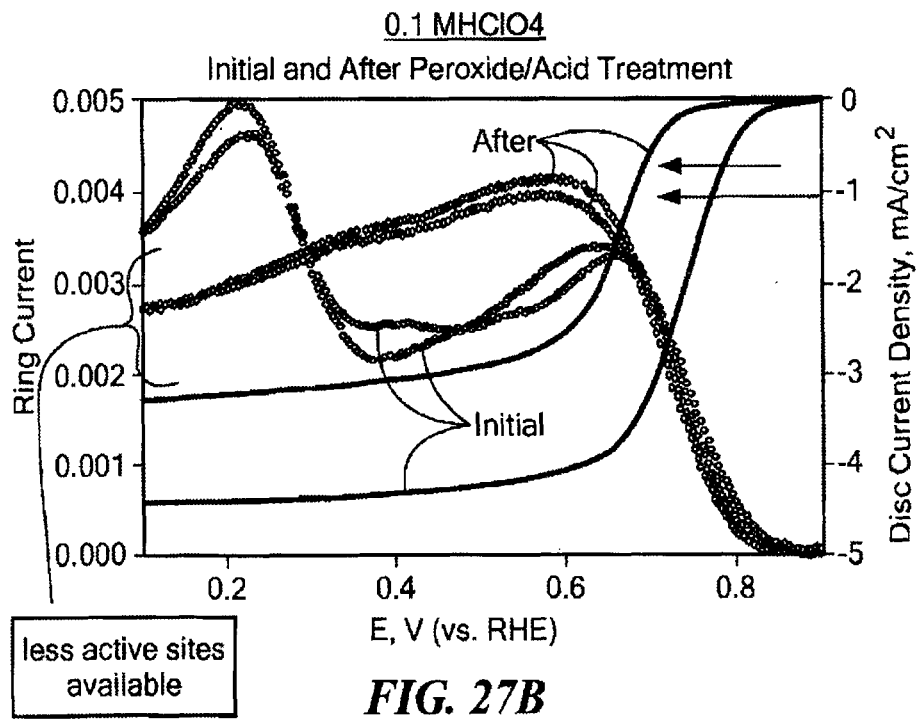
Figure 27C:
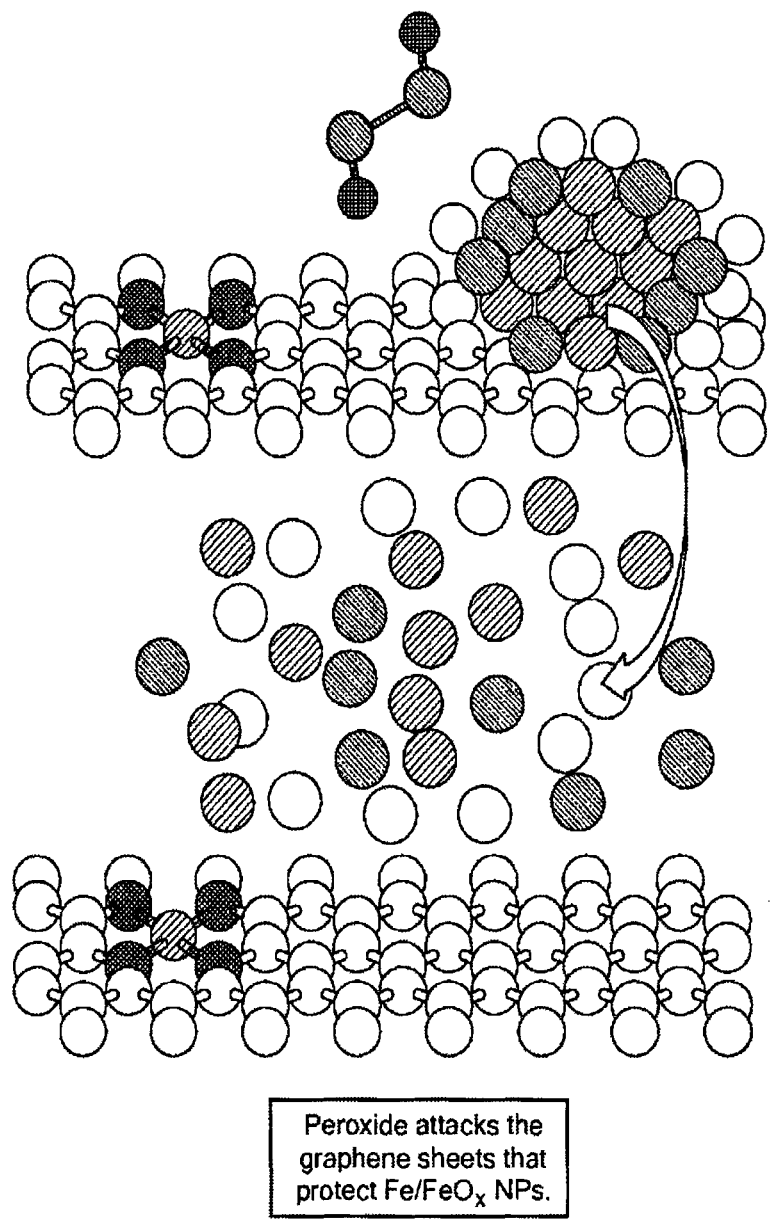
Figure 27D:
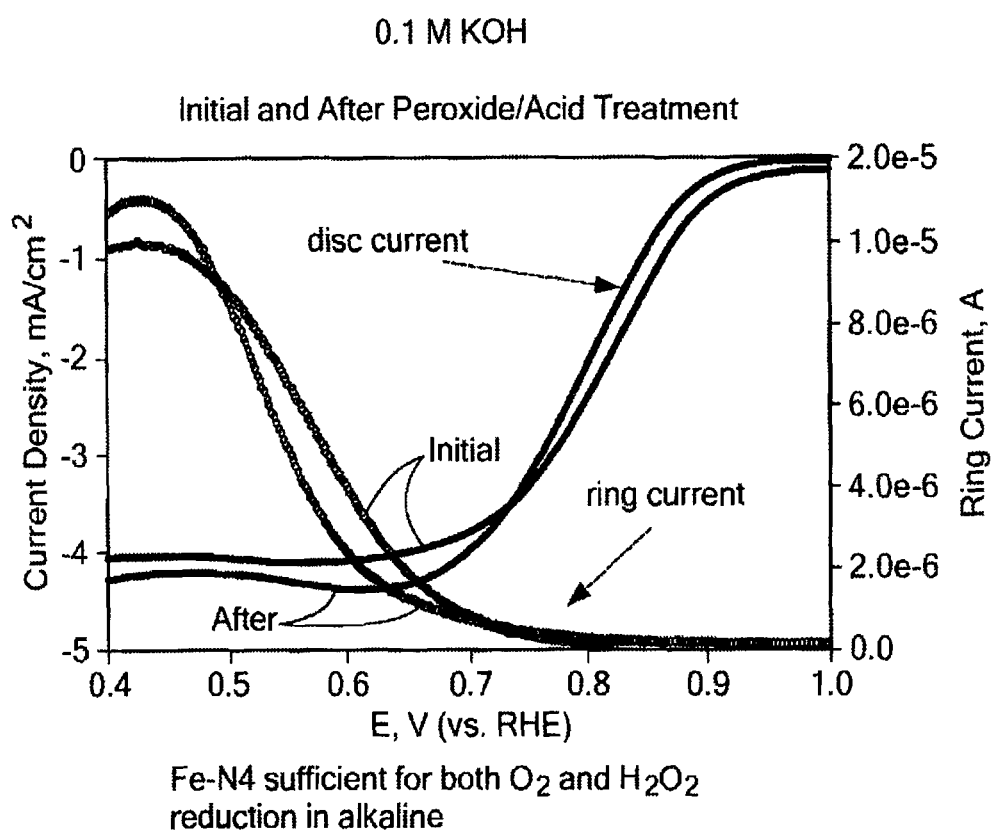
Figure 28A:
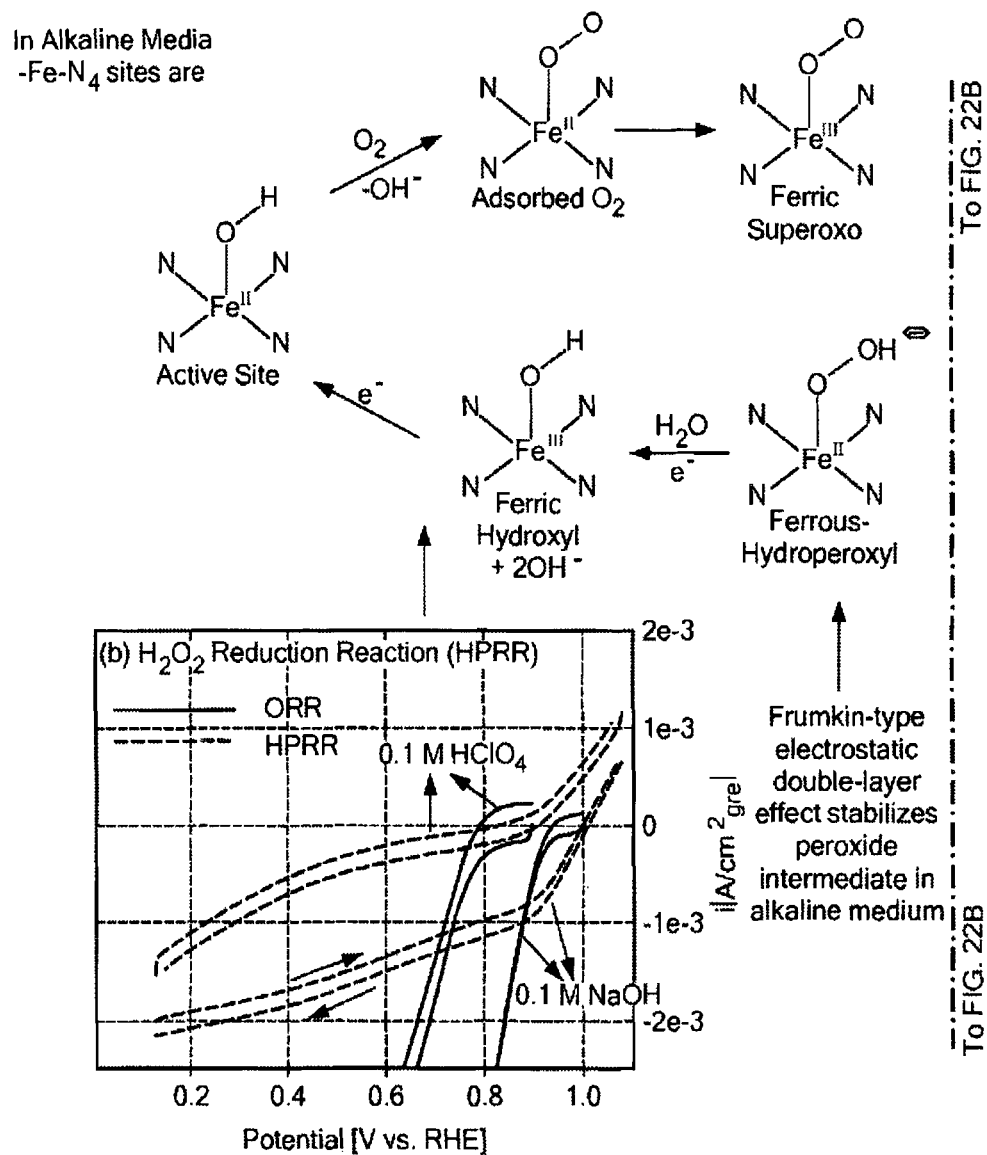
FIG. 28 is a schematic diagram for the mechanism of oxygen reduction reaction on Fe—$N_4$ sites in alkaline and in acidic media. In alkaline media Fe—$N_4$ sites are true 4e⁻ sites. In acidic media Fe—$N_4$ sites yield predominantly peroxide.
Figure 28B:
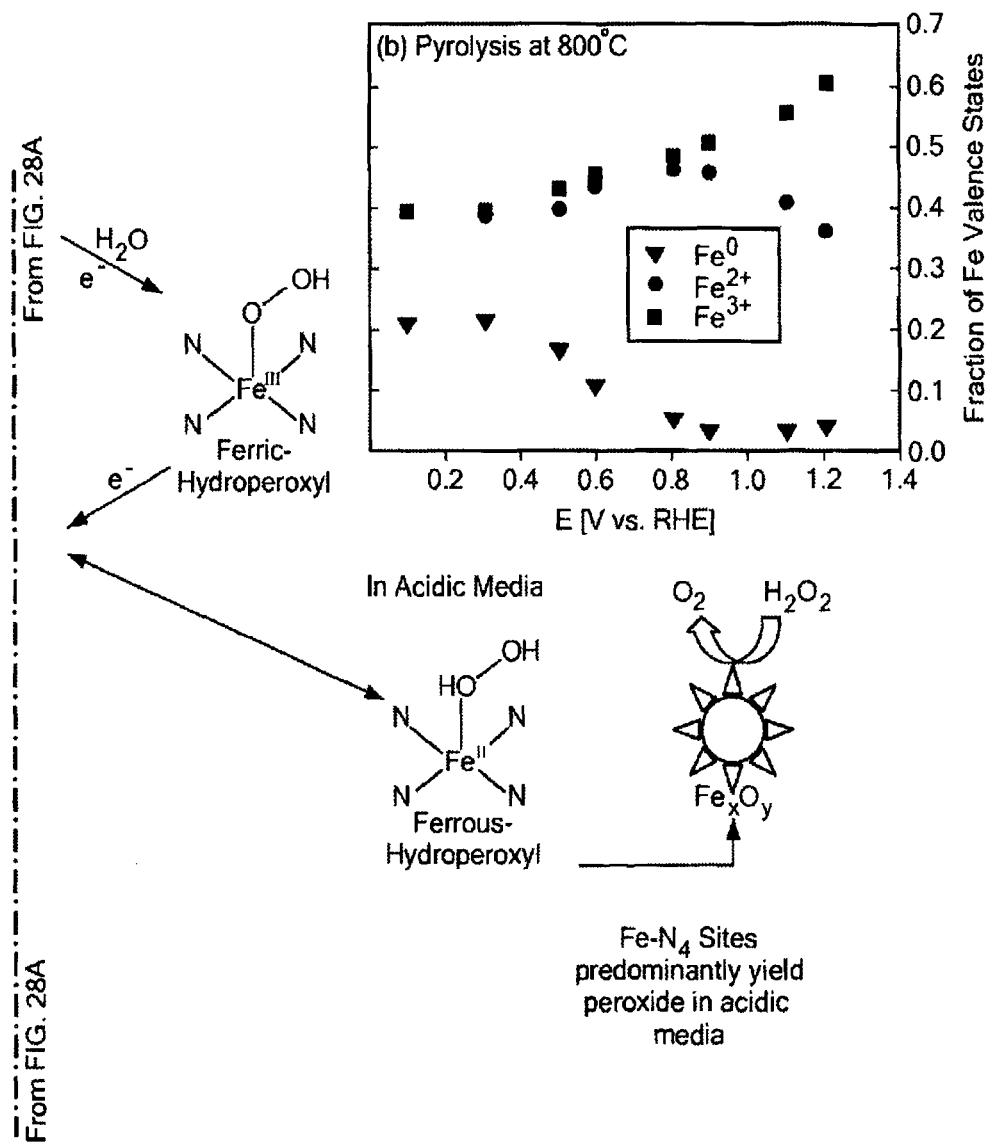
Figure 29A:
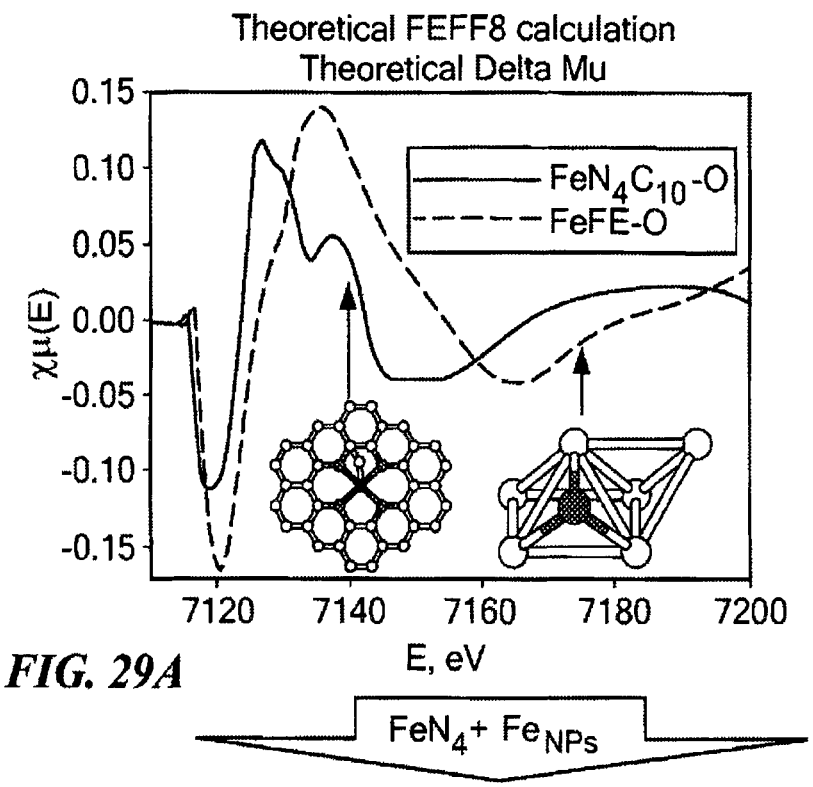
FIG. 29A-C is a set of graphs showing XANES spectra (Δμ) for the active centers in PolyMNC catalyst.
Figure 29B:
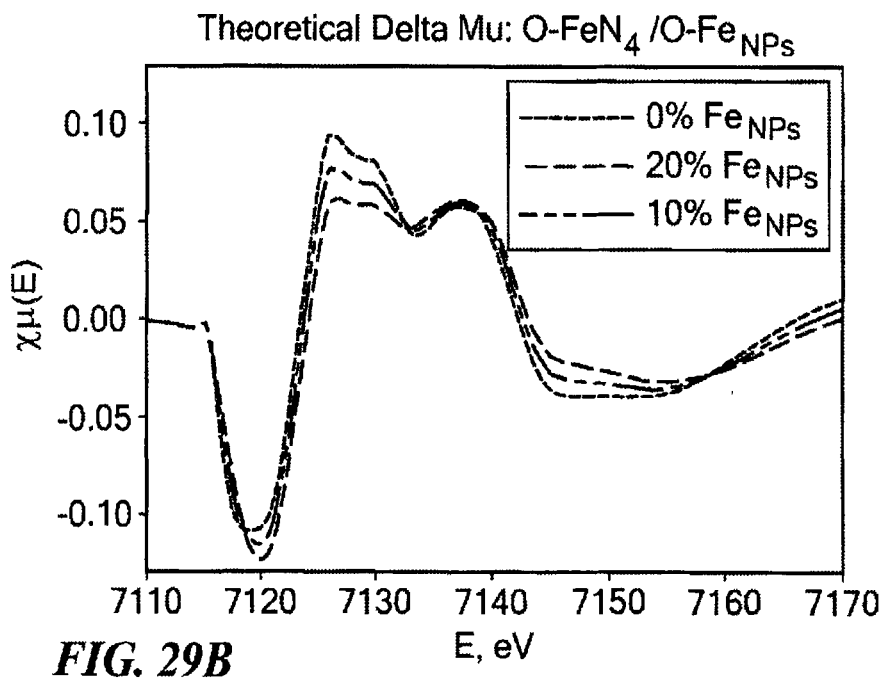
Figure 29C:
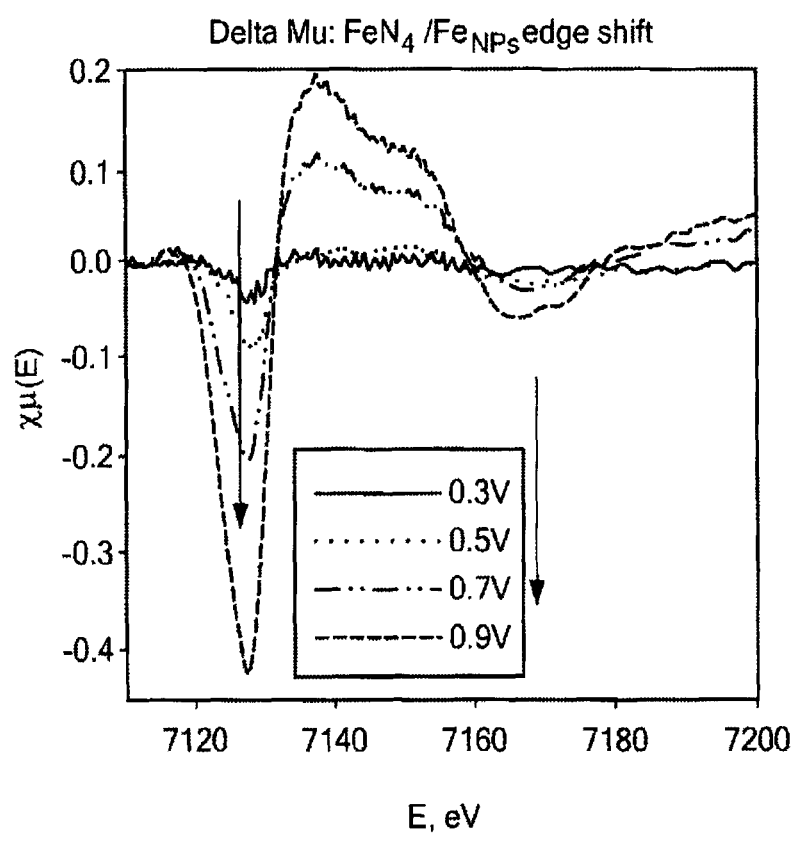
Figure 30:
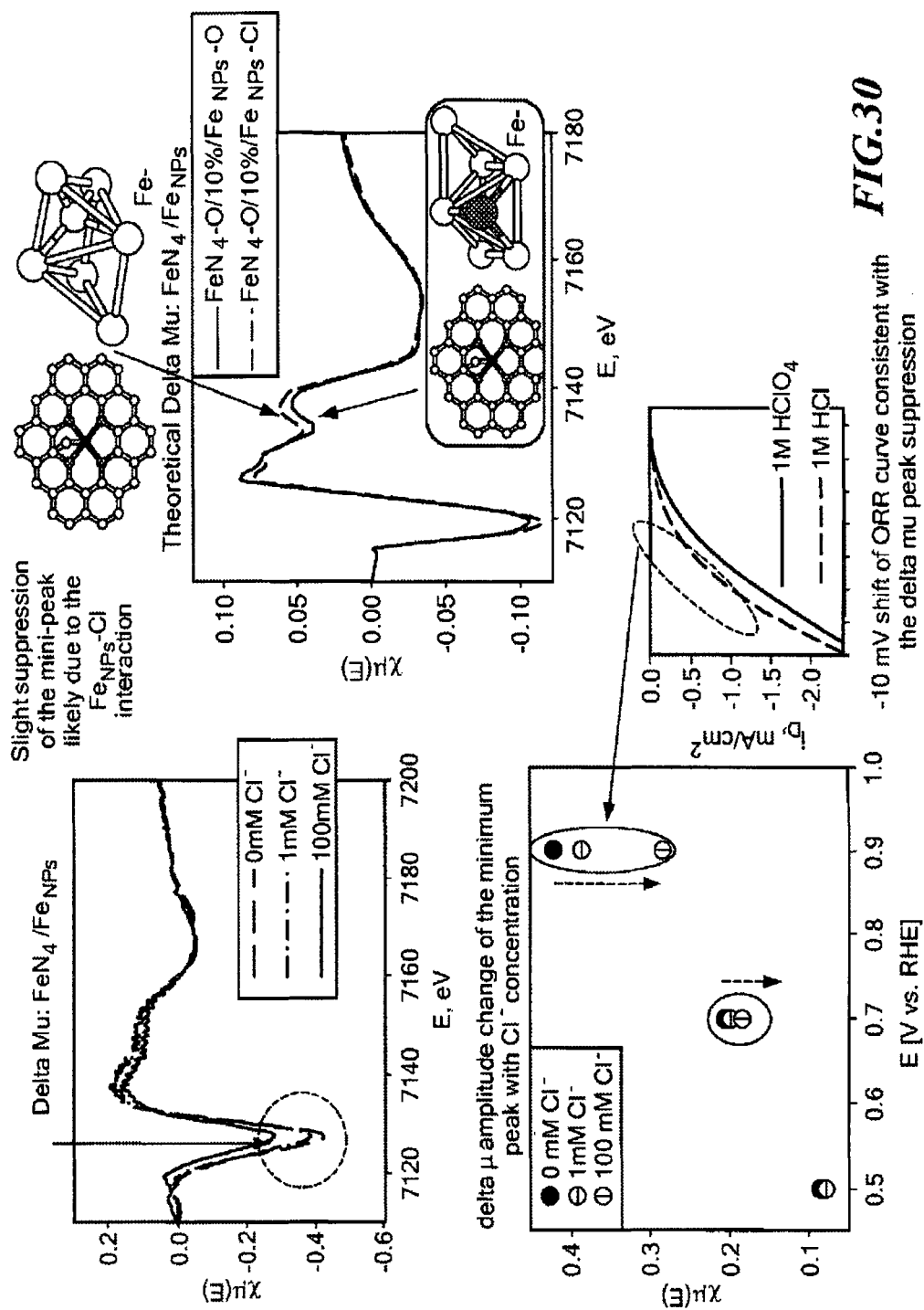
FIG. 30 is a set of graphs showing the behavior of M-$N_4$/$Fe_{NPs}$ sites in the presence of chloride ions. The upper left graph shows a slight suppression of the minimum-peak, which is likely due to the $Fe_{NPs}$Cl interaction. The graph at the right shows theoretical spectra for $FeN_4$/10% $Fe_{NPs}$—O and for $FeN_4$/10% $Fe_{NPs}$—Cl. The lower left graph shows a −10 mV shift of ORR curve consistent with Δμ peak suppression.
Figure 31A:
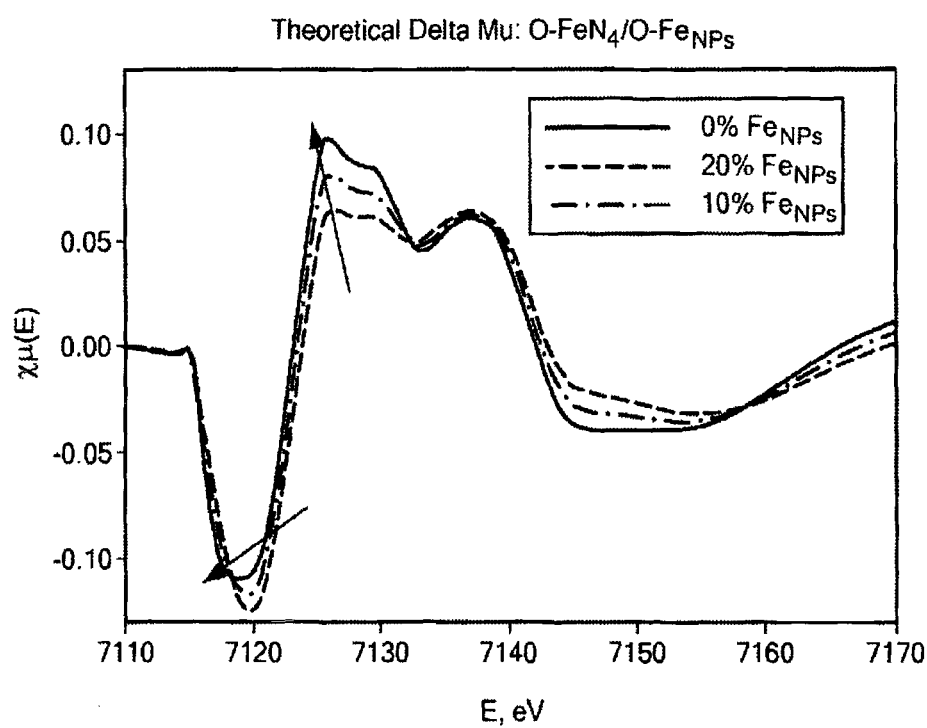
FIG. 31 is a set of graphs containing spectra showing the effect of selective removal of nanoparticles from M-$N_4$/$Fe_{NPs}$ electrocatalysts. Δμ changes upon removal of nanoparticles, which is consistent with theoretical models confirming participation of $Fe_{NPs}$ with O(H).
Figure 31B:
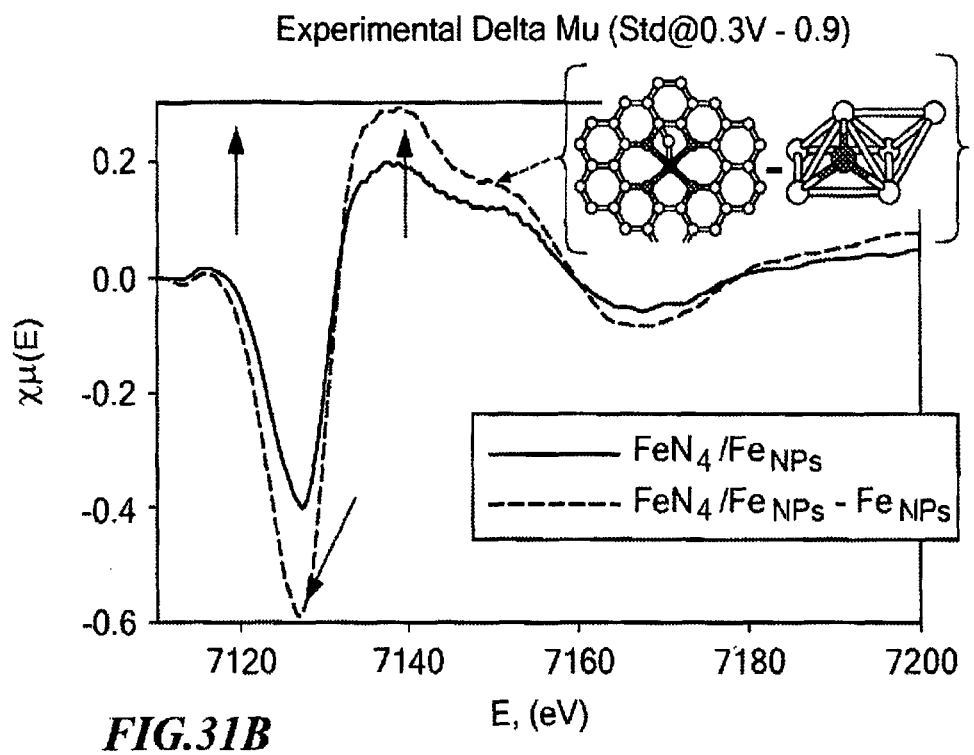
Figure 31C:
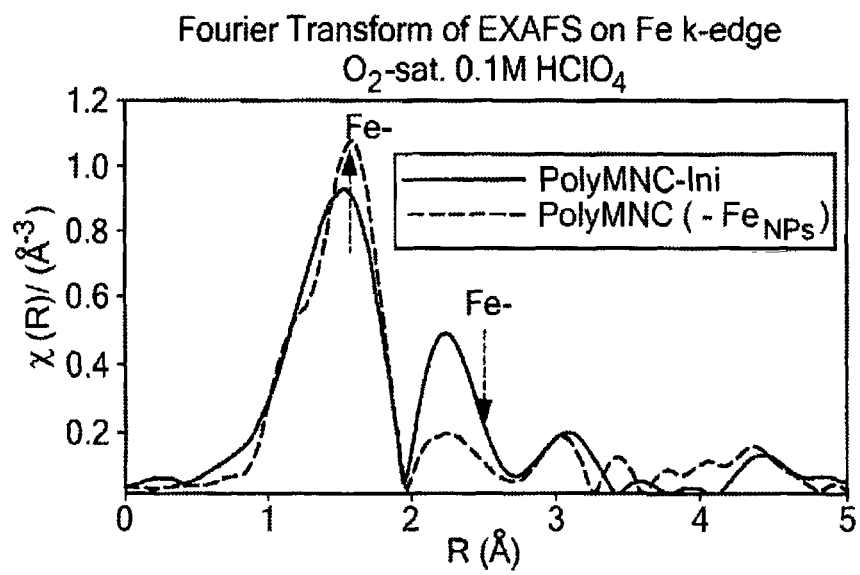
Figure 32:
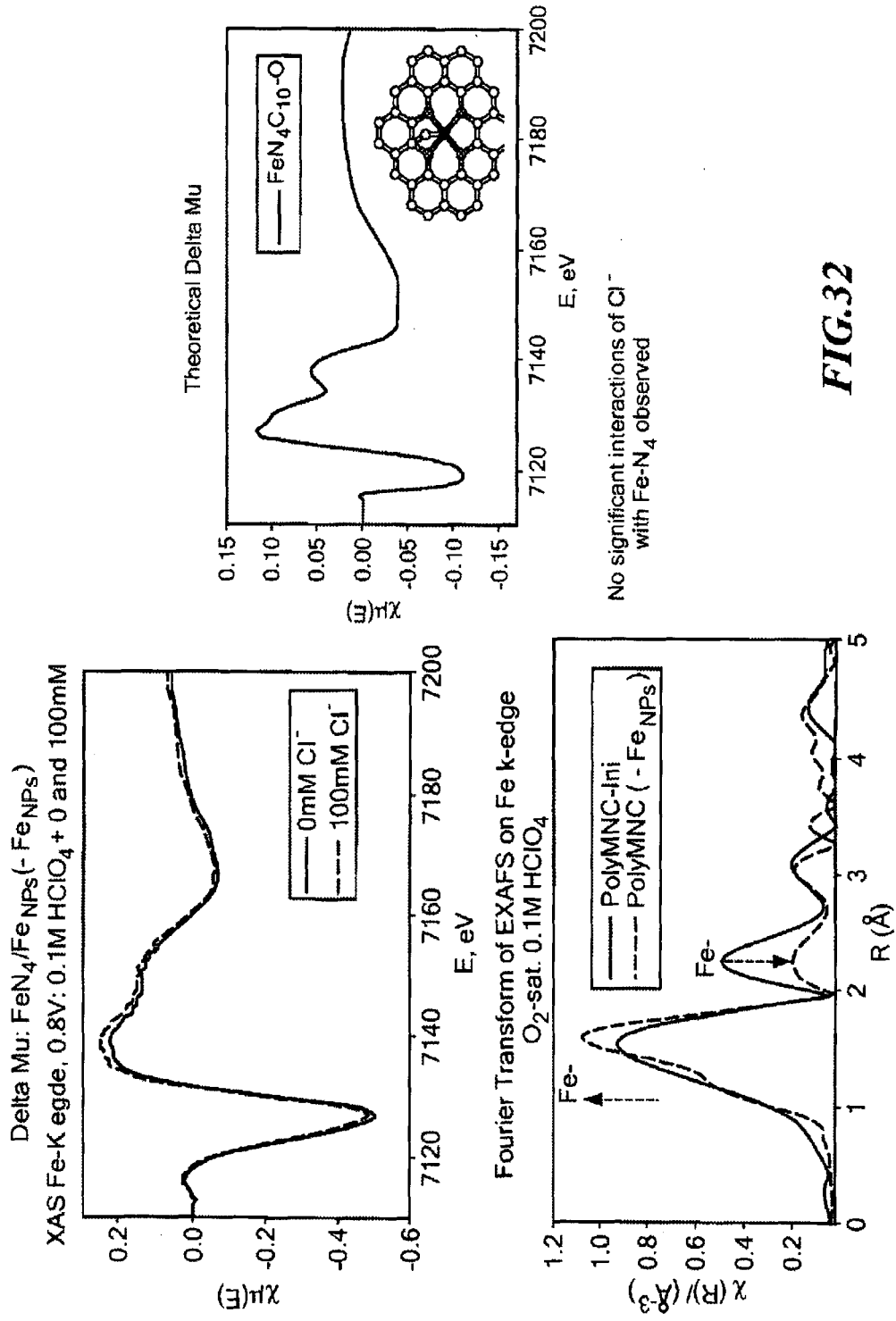
FIG. 32 is a set of graphs containing spectra of M-$N_4$/$Fe_{NPs}$ electrocatalysts showing resistance of M-$N_4$ sites to halides. No significant interaction of chloride ions with Fe—$N_4$ was observed.

Analysis of a variety of non-precious metal (NPM) electrocatalysts with X-ray absorption spectroscopy (XAS) showed that regardless of the synthetic technique and precursors used to the generate the electrocatalysts, they were found to have two characteristic scattering paths which differ only in prevalence. The encapsulated FeMOF is mostly comprised of FeNPs, indicated by the Fe—Fe scattering in the fourier transform plot (FIG. 19A). There is a minor contribution of a Fe—C/N/O scattering path. However XAS is unable to differentiate the exact nature of the element surrounding Fe due to their similar atomic number. That this catalyst is mostly comprised of Fe NPs is further supported by the absence of the Fe$^{2+}$/Fe$^{3+}$ edge shift in the x-ray-near-edge-spectrum (XANES) plot.

Figure 3C:
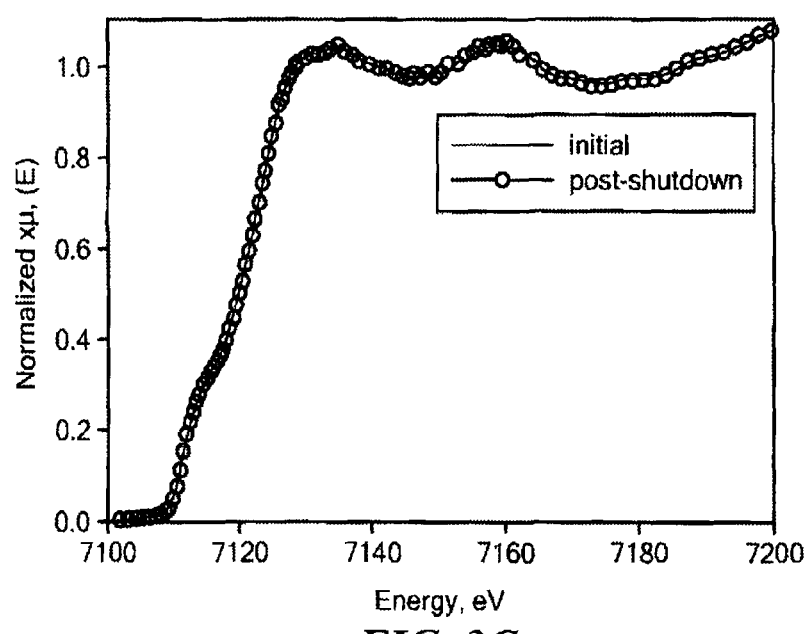
FIG. 3C is a XANES spectra of $Fe_xN_yC_z$ catalyst collected in-situ on Fe k-edge in 0.1M $HClO_4$ before and after the simulated shutdown.
Figure 4A:
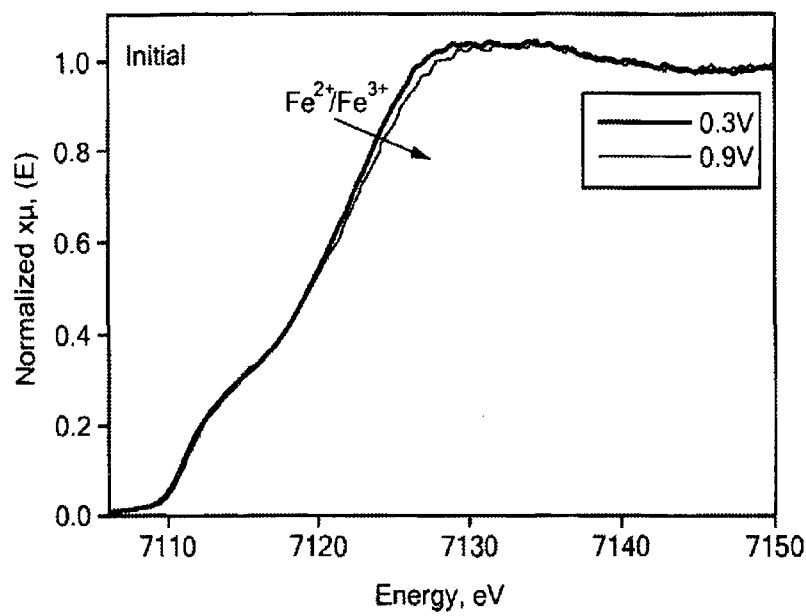
FIG. 4A and FIG. 4B are Fe K-edge Near Spectra (XANES) of $Fe_xN_yC_z$ catalysts collected in-situ at 0.1M $HClO_4$, at the initial stage and after exposure, respectively, to the simulated shut-down. The slight shift towards higher energy in both cases originates from $Fe^{2+}/Fe^{3+}$ transition of iron center in a Fe—$N_x$ moiety. The shift is maintained in the sample subjected to catastrophic shutdown, indicating that the Fe—$N_x$ center remained intact.
Figure 4B:
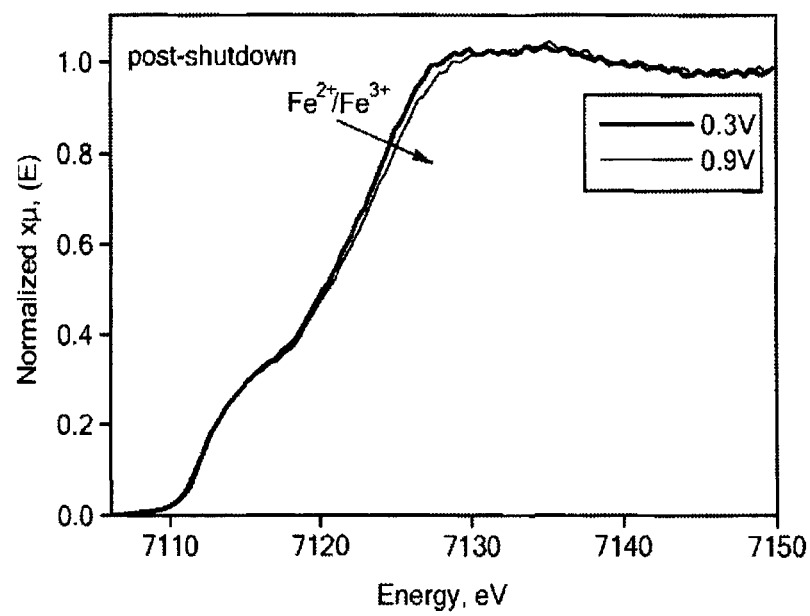
Figure 5:
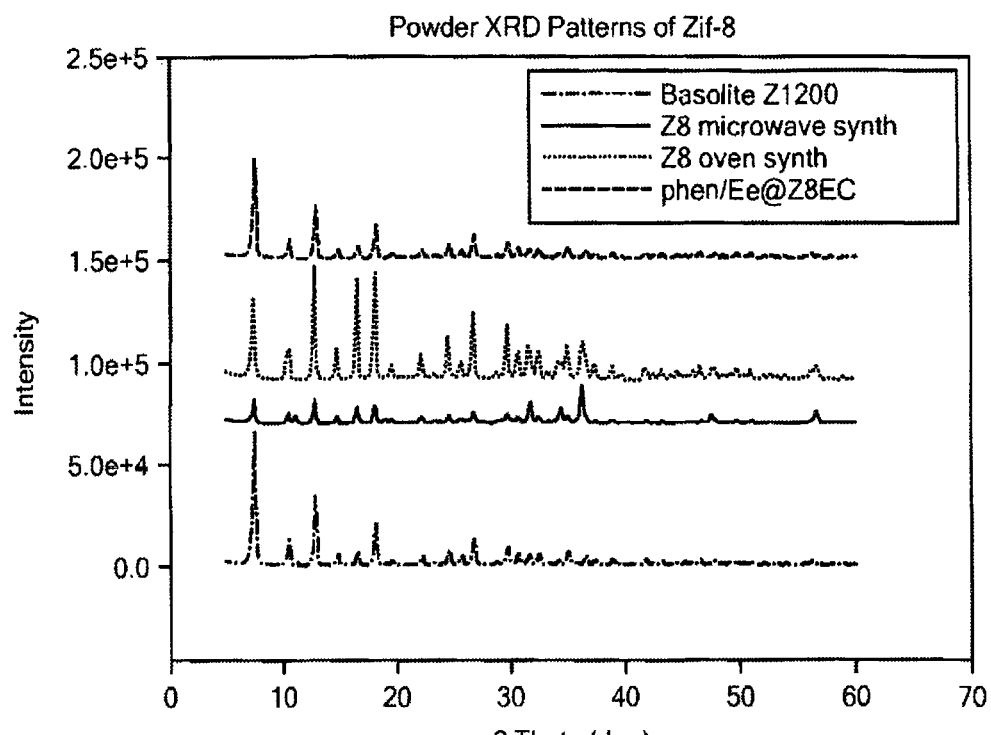
FIG. 5 is a set of powder X-ray diffraction patterns of different MOFs. Starting from the bottom the patterns are those of: Basolite Z1200©; Zeolitic imidazolate framework-8 (Zif-8) synthesized in microwave; Zif-8 synthesized in oven; and Zif-8 containing encapsulated phenanthroline/ Fe(OAc). The expected Zif-8 framework was not observed in Zif-8 containing exclusively iron (II) acetate.
Figure 6:
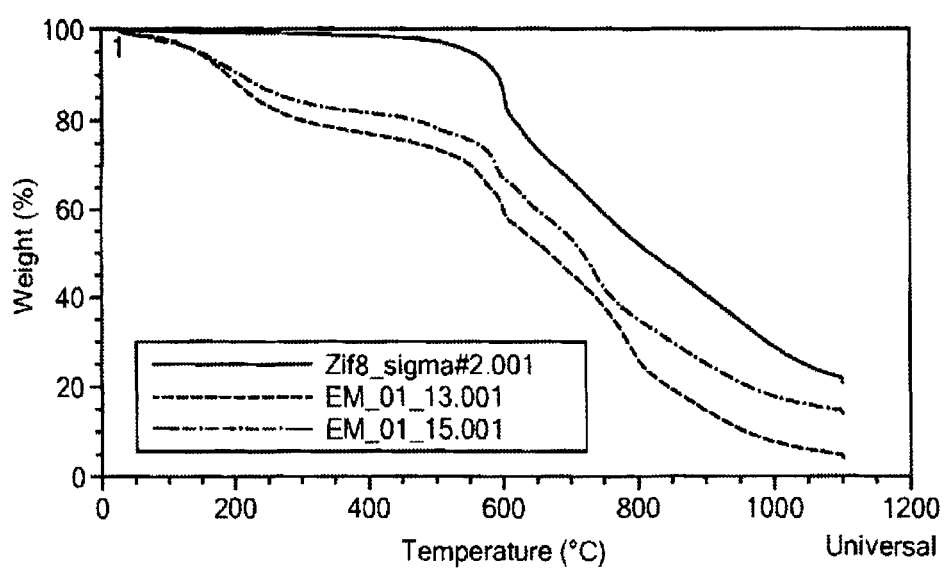
FIG. 6 is a set of traces from thermogravimetric analyses of Basolite Z1200© (top), microwave synthesized Zif-8 (middle), and oven synthesized Zif-8 (bottom; Yaghi, O. 2006).
Figure 7:
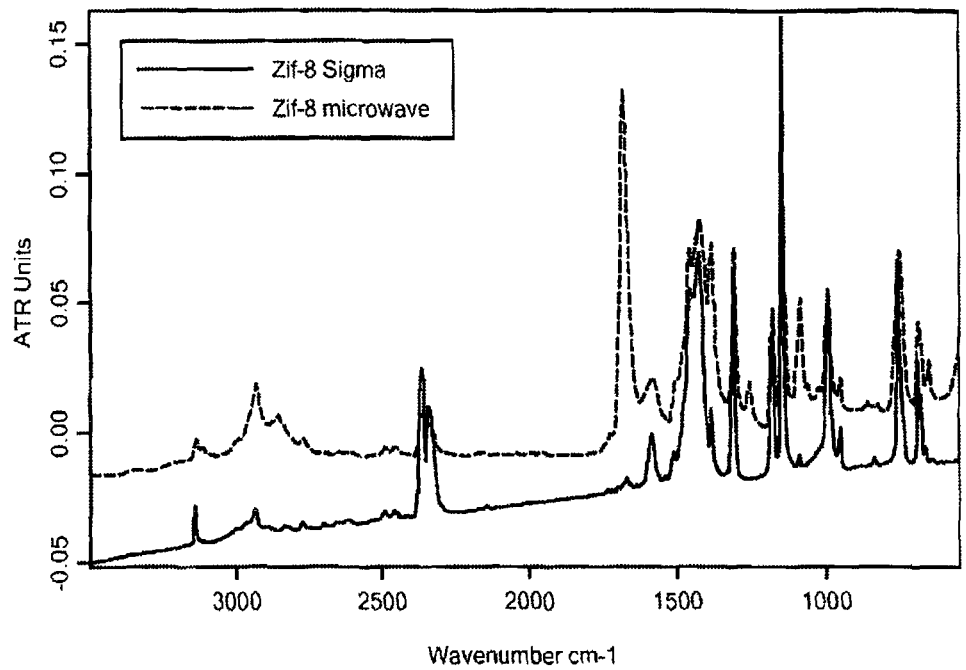
FIG. 7 shows infrared spectroscopy stretches of Basolite Z1200© (lower) and Zif-8 obtained by microwave synthesis (upper).
Figure 8:
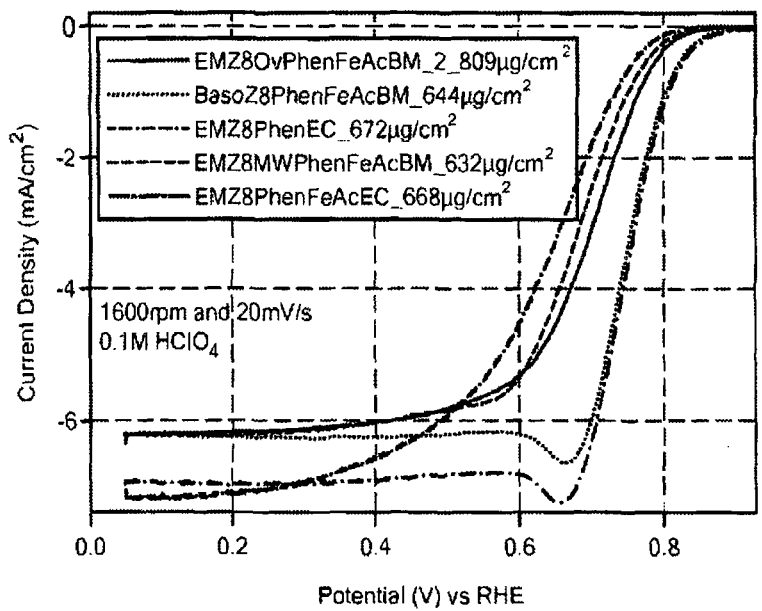
FIG. 8 is a set of traces of RDE measurements for: Zif-8 catalyst ball milled with catalytic active site precursors 1,10-phenanthroline monohydrate and iron(II) acetate; zif-8 having only 1,10-phenanthroline chemically encapsulated in the MOF pores; zif-8 having both 1,10-phenanthroline and iron(II) acetate chemically encapsulated in the MOF pores. The traces correspond to the catalysts: 1,10-phenanthroline chemically encapsulated in Zif-8 (first from top); iron(II) acetate (4% wt. iron) and 1,10-phenanthroline monohydrate ball milled with microwave synthesized Zif-8 (second from top); iron(II) acetate and 1,10-phenanthroline monohydrate ball milled with oven synthesized Zif-8 (third from top); Basolite Z1200© (Sigma Aldrich) ball milled (Proietti, E et al., 2011) with iron(II) acetate (4% wt. iron) and 1,10-phenanthroline monohydrate (fourth from top); and 1,10-phenanthroline and iron(II) acetate chemically encapsulated in Zif-8 (bottom trace).
Figure 9:
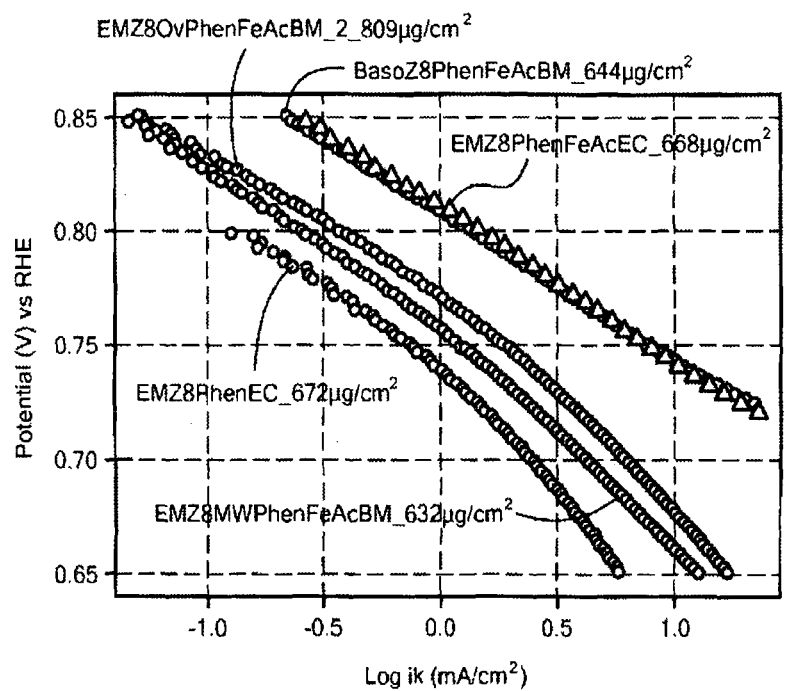
FIG. 9 is a set of Tafel plots of RDE measurements described in FIG. 8 for: Zif-8 catalyst ball milled with catalytic active site precursors 1,10-phenanthroline monohydrate and iron(II) acetate; zif-8 having only 1,10-phenanthroline chemically encapsulated in the MOF pores; zif-8 having both 1,10-phenanthroline and iron(II) acetate chemically encapsulated in the MOF pores. The plots correspond to the catalysts: 1,10-phenanthroline chemically encapsulated in Zif-8 (first from left); iron(II) acetate (4% wt. iron) and 1,10-phenanthroline monohydrate ball milled with microwave synthesized Zif-8 (second from left); iron(II) acetate (4% wt. iron) and 1,10-phenanthroline monohydrate ball milled with oven synthesized Zif-8 (third from left); Basolite Z1200© (Sigma Aldrich) ball milled (Proietti, E et al., 2011) with iron(II) acetate (4% wt. iron) and 1,10-phenanthroline monohydrate (extreme right; connected bead pattern); and 1,10-phenanthroline and iron(II) acetate chemically encapsulated in Zif-8 (extreme right; connected triangle pattern).
Figure 10:
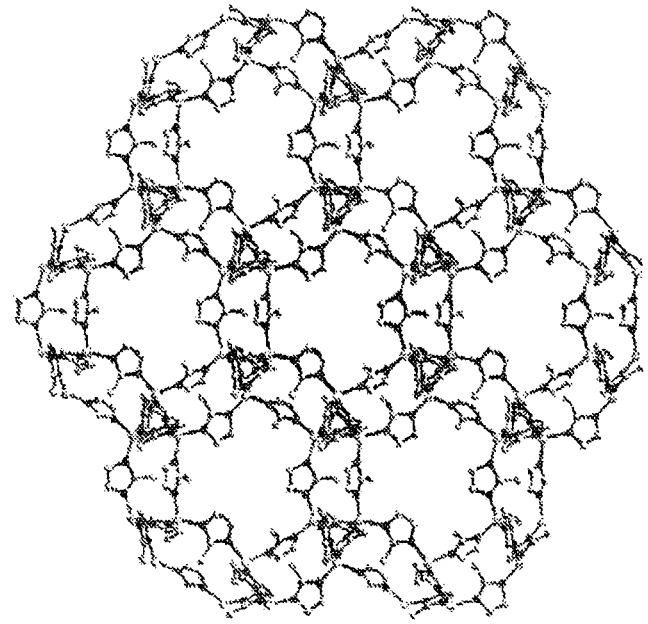
FIG. 10 is a diagram of the crystal structure of Zif-8. Light grey, dark, and grey spheres represent Zn, N, and C atoms, respectively. (Demessence, A. et al., 2010)
Figure 11:
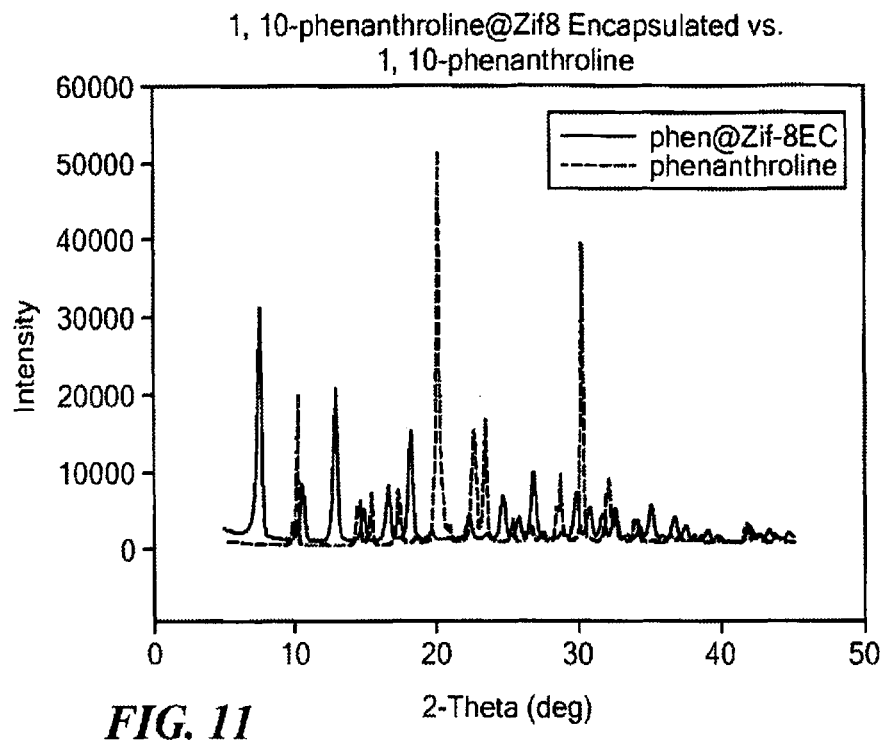
FIG. 11 is a pair of powder X-ray diffraction patterns of phenanthroline versus phenanthroline/Fe(OAc)$_2$@Zif-8. Lack of phenanthroline peaks in the MOF (dark) support encapsulation rather the free phenanthroline (light) in the sample.
Figure 12:
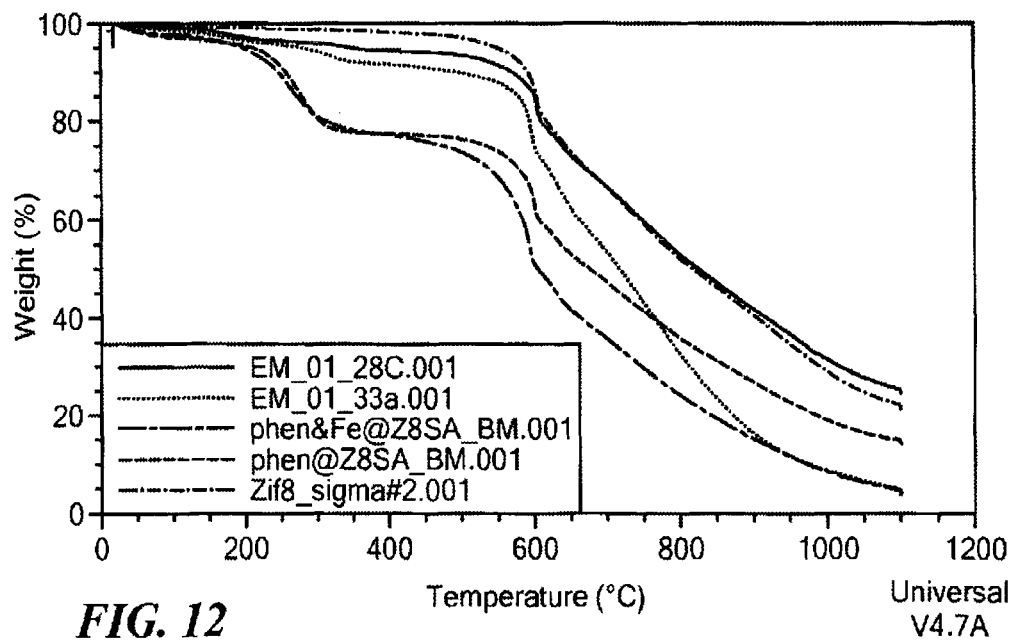
FIG. 12 is a set of traces from thermogravimetric analyses of: 1,10-phenanthroline chemically encapsulated in Zif-8 (second from top); phenanthroline/Fe(OAc)$_2$ chemically encapsulated in Zif-8 (third form top); 1,10-phenanthroline chemically encapsulated in Zif-8 (fourth from top) and ball milled; phenanthroline/Fe(OAc)$_2$ chemically encapsulated in Zif-8 and ball milled (fifth form top); Basolite Z1200© (first from top).
Figure 13:
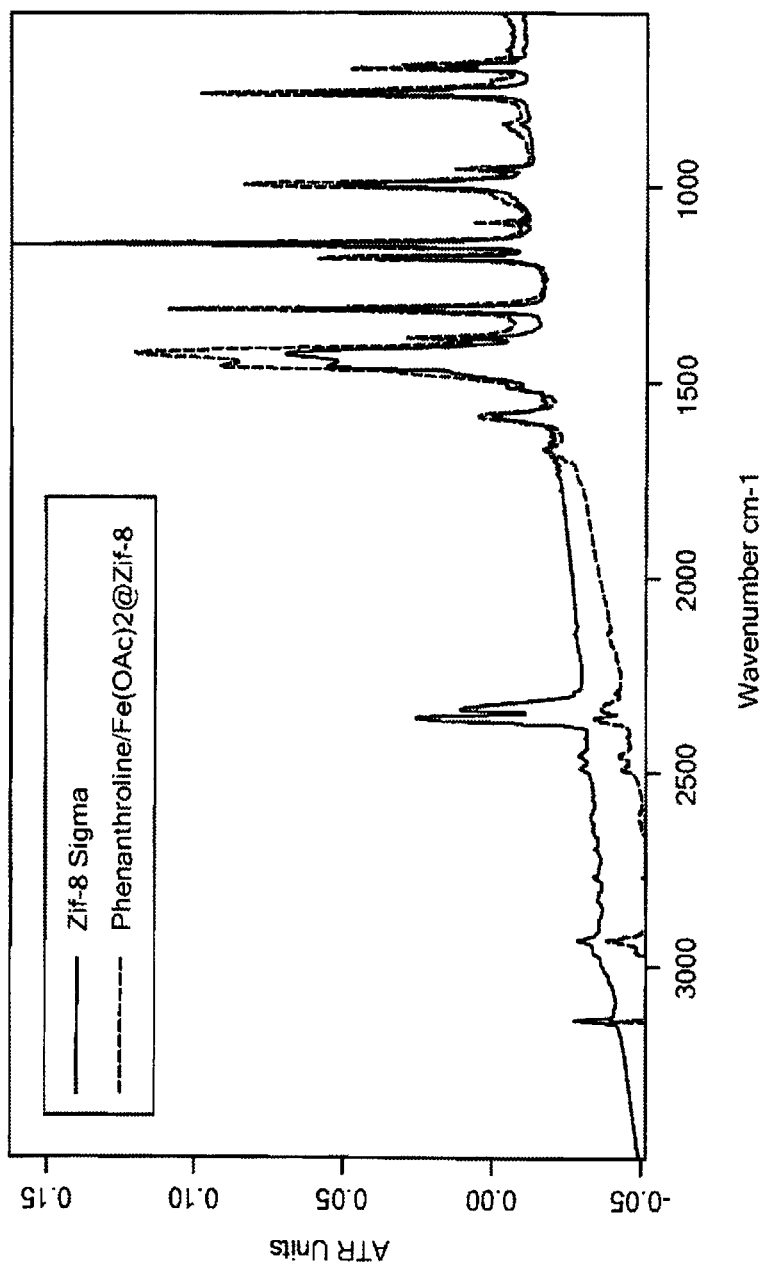
FIG. 13 is a pair of infrared spectroscopy stretches of Basolite Z1200© (upper trace) and phenanthroline/Fe (OAc)$_2$ chemically encapsulated in Zif-8 (lower trace).
Figure 17:
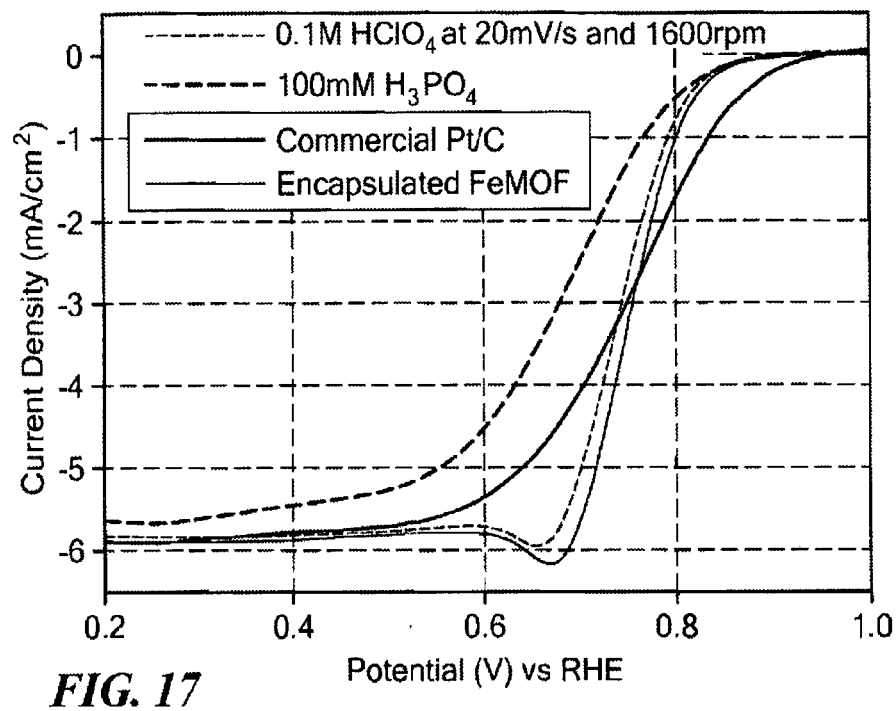
FIG. 17 is a comparison of RDE voltammograms of ORR at encapsulated FeMOF with those at Pt/C in 0.1M HClO$_4$ with or without the addition of 100 mM H$_3$PO$_4$. Current density was based on normalization of voltammetric current to the geometrical area of the electrode. Rotation rate: 1600 rpm; Scan rate 20 mV/s.
Figure 18:
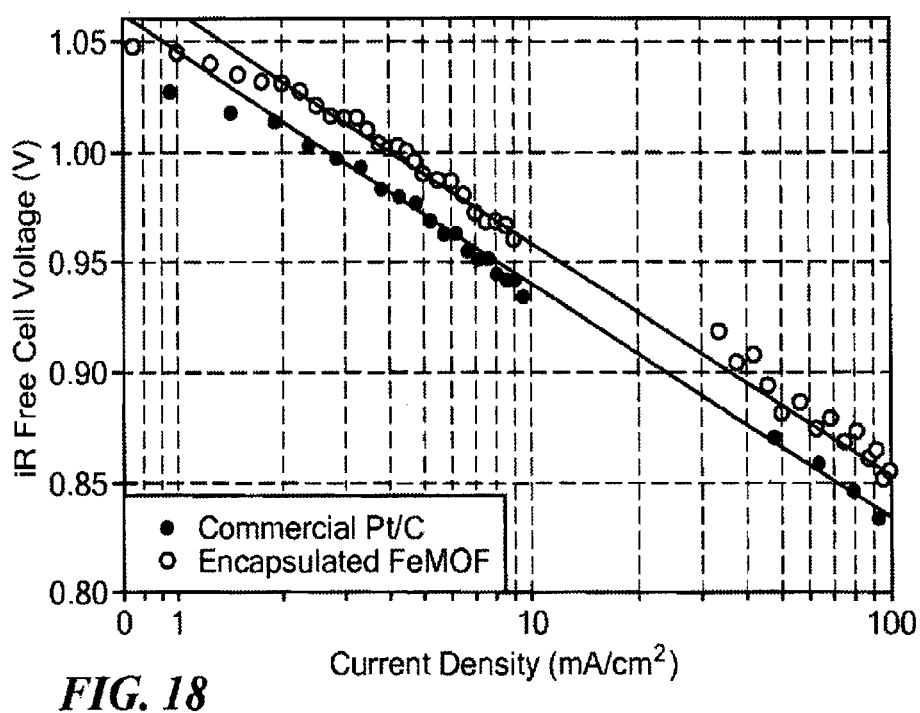
FIG. 18 is a comparison of polarization curve obtained from a fuel cell having encapsulated FeMOF (upper) with that obtained from commercial Pt/C (lower), in phosphoric acid as the membrane electrolyte at 180° C. with H$_2$/O$_2$. The FeMOF catalyst containing fuel cell shows a performance similar to the Pt/C catalyst containing cell.

The immunity of the MNC catalysts described here to chloride ion originates mainly from the unique nature of the metal-based active site that dominate in these catalysts. In some embodiments, the catalyst contains highly active and corrosion resistant nanoparticles. In general, the MOF-derived FeNC catalyst described here consists of two main types of metal centers. The majority of metal centers are crystalline phase Fe$_x$N$_y$C$_z$ nanoparticles, and amorphous Fe—N$_4$ centers incorporated into carbon cavity (FIG. 2D). Neither metal center is affected by chloride anions (FIG. 3). This is represented by RDE ORR polarization curves (FIG. 2A) and the corresponding in-situ X-ray Absorption Spectroscopy (XAS) spectra of the catalyst (FIG. 3C). Both metal species sustain their catalytic structure even after being subjected to flooding with hot 5M hydrochloric acid (5M HCl), resulting in the catastrophic shutdown.

Further provided by the invention are expedited synthetic routes to non-platinum group (non PGM) electrocatalysts suitable for application to ORR. The synthesis of the electrocatalysts of the invention involves the synthesis of MOFs. Previously established syntheses of MOFs have required solvothermal reaction between an organic ligand and a transition metal salt dissolved in an organic solvent. Typical reaction run times of previously described syntheses range from 24-72 h in a programmable furnace tube (or other source of controlled heat) heated at 100-180° C. The reaction product had to be subsequently washed with an organic solvent to provide the porous framework of the MOF in crystalline form (Yaghi, 2006). In previous methods the MOFs had to be manually mixed with a nitrogen-containing catalytic active site precursor and a metal source external of the framework for incorporation into the MOF infrastructure during manual mixing (Proietti, E. 2011). The product was then made conductive by pyrolysis at 900-1200° C. and the activated material was coated onto the fuel cell cathode to catalyze four electron oxygen reduction to water. Preparation of such catalysts previously required multiple lengthy steps including a one to three day synthesis of the framework itself (Yaghi, 2006). Manual mixing of the catalytic precursors (metal salt and nitrogen-containing organic molecule) into the MOF pores resulted in lack of sample homogeneity with respect to the transition metal, resulting in poorer catalytic properties. The step of mixing was accompanied by significant potential for incorporation of impurities into the sample.

The problem of multiple lengthy steps and manual mixing have been overcome by two distinct synthetic routes of the present invention: (1) microwave-accelerated synthesis of the MOF, and (2) one-pot MOF formation-catalytic precursor encapsulation. The resulting products have shown RDE results comparable to that of catalysts derived from previously established methods.

The benefits of using the methods of synthesis described here over earlier methods include: (1) shortening of reaction time for MOF synthesis from days to hours or minutes; (2) chemical encapsulation of catalytic active site precursors for ORR during the synthesis as opposed to crude mixing of precursors into the MOF pores, resulting in a cleaner product with more effective active sites; (3) less equipment required; and (4) use of ambient conditions. The synthetic methods of the present invention also can be applied to expedited syntheses of metal organic frameworks for other uses.

As an example of the synthesis of a MOF using microwave-accelerated synthesis, zeolitic imidazole framework-8 (Zif-8) was produced, and the product characterized and confirmed with powder X-ray diffraction (PXRD), thermogravimetric analysis (TGA), and infrared spectroscopy (IR), and analyzed with scanning electron microscopy (SEM), energy dispersion detection (EDS), and rotating disc electrode (RDE) apparatus.

MOF was also synthesized with simultaneous chemical encapsulation of catalytic precursors. The complete synthesis was carried out in one pot, in contrast to the traditional procedure in which MOF is synthesized in a first step, and is subsequently mixed manually with the catalytic precursors in a second step. In the traditional method, following a multi-day synthesis of the metal organic framework, the MOF has to be violently ball milled for 1-5 hours with the dry catalytic precursors to incorporate them into the framework matrix. Such mixing, even at lengthy run times, does not ensure homogeneous distribution of the precursors into the MOF, and cannot ensure that the precursors enter the MOF pores, as opposed to being simply distributed on the MOF surface.

Chemical encapsulation made possible by the one-pot MOF formation-chemical precursor encapsulation described here (Example 2) ensures more homogenous distribution of the catalytic precursors into the MOF pores compared to mixing pre synthesized MOF with catalytic precursors by ball milling. Further, since both the MOF synthesis and the precursor encapsulation can be accomplished in the same pot, there is less opportunity for sample contamination. Further still, since the pores form around the precursors, there is a greater opportunity for the precursors to be captured inside of the pores compared to the use of manual mixing or ball milling of a pre formed MOF with catalytic precursors.

EXAMPLES

Example 1: Synthesis of Zif-8 MOF Using Microwave-Accelerated Synthesis

For the synthesis of Zif-8, zinc nitrate tetrahydrate (1.1 equivalence) and 2-methylimidazole (1 equivalence) were combined in a glass microwave tube and dissolved in dimethylformamide (1 mL/1.67E-4 mol combined starting material). The tube, equipped with a stir bar, was capped and heated to 140° C. (same temperature as conventional furnace synthesis) with stirring for 40 minutes. A white or light yellow crystalline powder was afforded upon washing with chloroform and filtering the heated material. The product was dried to yield the MOF material.

The reaction time was significantly shorter than that required in the conventional furnace synthesis. For example, the furnace synthesis of Zif-8 reaction requires over 24 h not including a ramp rate of 5° C./min 22-140° C. and a subsequent cooling rate of 0.4 C/min back to room temperature from 140° C. In contrast, microwave accelerated Zif-8 synthesis occurred with a 2 min ramp rate to 140° C., 45 min run time, and 10 min cooling time. The microwave reaction times can be expected to differ depending on the relative length of conventional heating time of the MOF.

Once activated, the MOF was suitable for use as a cathodic catalyst for four electron reduction of oxygen to water, or further two electron reduction of hydrogen peroxide reduction to water in a fuel cell.

Example 2: Synthesis of Zif-8 MOF with Encapsulation of Catalytic Precursors in One Pot The one-pot Zif-8 MOF formation-precursor encapsulation synthesis was carried out as shown in the scheme below.

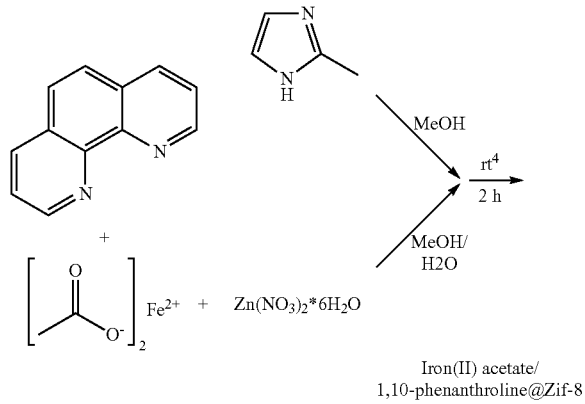

In flask A, 2-methylimidazole (160 equivalence) was dissolved in methanol with stirring (1 mL/1.60E-4 mol). In flask B, zinc nitrate tetrahydrate (80 equivalence) and 1,10-phenanthroline monohydrate (160 equivalence) were dissolved in a 1/1.2 v/v mixture of water/methanol (1 mL/0.002 mol combined reagents) with stirring. Once fully dissolved, flask B solution was poured into flask A solution, and iron(II) acetate (1 equivalence) was added to the stirring mixture. This was capped and stirred at room temperature for 2 h-24 h until a white precipitate formed. See Liedana 2012 for reaction condition details. The reaction contents were centrifuged at 4000 rpm for 30-60 min, washed with methanol, and centrifuged again, then dried to afford a powdery pellet of product.

REFERENCES

Demessence, A. *J. Mater. Chem.* 2010. 20, 7676.
He, Q. *Phys Chem Chem Phys.* 2010, 12, 12544.
Jaouen, F., Proietti, E., Lefevre, M., Chenitz, R., Dodelet, J. P., Wu, G., Chung, H. T., Johnston, C. M., Zelenay, P., Recent advances in non-precious metal catalysis for oxygen-reduction reaction in polymer electrolyte fuel cells. *Energ Environ Sci* 2011, 4 (1), 114-130.
Liedana, N. *ACS Appl. Mater. Interfaces.* 2012. 4, 5016.
Olson, T. Pylypenko, S., Fulghum, J., Atanassov, P., *J. Electrochem. Soc.,* 157 (2010) B54-B63.
Proietti, E. *Nat. Commun.* 2011. 2, 416.
Shah, R. K., Introduction to Fuel Cells, In *Recent Trends in Fuel Cell Science and Technology,* Basu, S., Ed. Anamaya Publishers: 2007.
Wu G, More K L, Johnston C M, Zelenay P. High-performance electrocatalysts for oxygen reduction derived from polyaniline, iron, and cobalt. *Science,* 2011 Apr. 22; 332(6028):443-7.
Yaghi, O. *Proc. Natl. Acad. Sci.* 2006. 103, 10186.

What is claimed is:

1. A method of synthesizing an electrocatalyst for an oxygen reduction reaction, the method comprising the steps of:
   (a) reacting an organic ligand, a first transition metal or salt thereof, and a first catalytic precursor to form a product, wherein the first catalytic precursor is a heteroatom-containing organic molecule, and wherein the product comprises a metal organic framework (MOF) comprising the first transition metal;
   (b) reacting a second catalytic precursor with the product resulting from (a) until a precipitate is formed, wherein the second catalytic precursor is a second transition metal or salt thereof, whereby the first and the second catalytic precursors are encapsulated inside the MOF; and
   (c) isolating the precipitate and subjecting it to pyrolysis, whereby the first transition metal evaporates yielding the electrocatalyst.

2. The method according to claim 1, wherein the heteroatom-containing organic molecule provides a heteroatom capable of catalyzing an oxygen reduction reaction.

3. The method according to claim 1 wherein the pyrolysis is carried out at about 700° C. to about 1100° C.

4. The method according to claim 1, wherein the heteroatom-containing organic molecule comprises one or more heteroatoms selected from the group consisting of nitrogen, oxygen, and sulfur.

5. The method according to claim 1, wherein the second transition metal is a non-noble transition metal.

6. The method according to claim 5, wherein the non-noble transition metal is selected from the group consisting of iron, cobalt, copper, nickel, and chromium.

7. The method according to claim 1, wherein the first and the second transition metals have oxidation states selected from the group consisting of all known oxidation states for the respective transition metal.

8. The method according to claim 1, wherein the first transition metal is zinc.

9. The method according to claim 1, wherein the salt of each of the first and the second transition metals is selected from the group consisting of acetate, nitrate, sulfate, phosphate, and chloride.

10. The method according to claim 1, wherein the organic ligand is selected from the group consisting of imidazole, methylimidazole, pyridine, pyridine derivatives, pyrimidine, triazole, tetrazole, napthylene, and napthyridine.

11. The method according to claim 1, wherein the second transition metal is in the form of nanoparticles or a colloid accommodated within pores of the MOF.

12. The method according to claim 1, wherein the first catalytic precursor is selected from the group consisting of phenanthroline, porphyrin, imidazole, pyridine, pyrimidine, and triazole.

13. The method according to claim 1, wherein the electrocatalyst is cross-linked as a result of the pyrolysis in step (c).

14. The method according to claim 1, wherein the electrocatalyst is resistant to anion poisoning when used in an oxygen reduction reaction.

15. An electrocatalyst comprising graphene sheets and a transition metal, wherein the graphene sheets consist of carbon atoms and heteroatoms, and wherein the transition metal is coordinated with the heteroatoms.

16. The electrocatalyst according to claim 15, further comprising nanoparticles, the nanoparticles comprising or consisting of a non-oxidated metal (M) surrounded with a layer of metal oxide ($M_xO_y$).

17. A cathode for an electrolytic process for chlorine evolution in a chlor-alkali electrolysis cell, the cathode comprising the electrocatalyst according to claim 15.

18. A cathode for an electrolytic process for chlorine evolution in an HCl electrolyzer, the cathode comprising the electrocatalyst according to claim 15.

19. A cathode for a phosphoric acid fuel cell comprising the electrocatalyst according to claim 15.

20. A cathode for carrying out an oxygen reduction reaction in an electrolytic process, the cathode comprising the electrocatalyst of claim 15, wherein the cathode is resistant to anion poisoning.

21. The cathode according to claim 20 that is resistant to poisoning by chloride ion.

22. The cathode according to claim 20 that is resistant to poisoning by dihydrogen phosphate ion.

23. A method of chlorine evolution, the method comprising the step of electrolyzing brine in a chlor-alkali electrolysis cell, wherein the cathode of the cell comprises the electrocatalyst according to claim 15.

24. A method of chlorine evolution comprising electrolyzing HCl in an HCl electrolyzer, wherein the cathode of the electrolyzer comprises the electrocatalyst according to claim 15.

25. The method according to claim 1, wherein steps (a) and (b) are carried out in a single reaction vessel.

* * * * *